(12) United States Patent
Winter et al.

(10) Patent No.: US 12,193,795 B2
(45) Date of Patent: Jan. 14, 2025

(54) CONTACTLESS SENSOR-DRIVEN DEVICE, SYSTEM, AND METHOD ENABLING AMBIENT HEALTH MONITORING AND PREDICTIVE ASSESSMENT

(71) Applicant: Norbert Health, Inc., Brooklyn, NY (US)

(72) Inventors: Alexandre G. Winter, Brooklyn, NY (US); Jonathan Platkiewicz, Boulogne-Billancourt (FR)

(73) Assignee: Norbert Health, Inc., Brooklyn, NY (US)

( * ) Notice: Subject to any disclaimer, the term of this patent is extended or adjusted under 35 U.S.C. 154(b) by 582 days.

(21) Appl. No.: 17/225,313

(22) Filed: Apr. 8, 2021

(65) Prior Publication Data
US 2021/0315467 A1     Oct. 14, 2021

Related U.S. Application Data

(60) Provisional application No. 63/119,015, filed on Nov. 30, 2020, provisional application No. 63/007,983, filed on Apr. 10, 2020.

(51) Int. Cl.
*A61B 5/0205* (2006.01)
*A61B 5/00* (2006.01)
*A61B 5/103* (2006.01)

(52) U.S. Cl.
CPC ........ *A61B 5/02055* (2013.01); *A61B 5/0004* (2013.01); *A61B 5/1032* (2013.01);
(Continued)

(58) Field of Classification Search
CPC . A61B 5/0531; A61B 5/02416; A61B 5/1171; A61B 10/0012; A61B 2010/0019;
(Continued)

(56) References Cited

U.S. PATENT DOCUMENTS 9,520,051 B1   12/2016   Zack et al.
9,568,594 B2   2/2017    Harash et al.
(Continued)

FOREIGN PATENT DOCUMENTS

WO   2019089830 A1   5/2019

OTHER PUBLICATIONS

International Search Report and Written Opinion for PCT/US2021/026755 mailed Jul. 30, 2021, 12 pages.
(Continued)

*Primary Examiner* — Ajibola A Akinyemi
(74) *Attorney, Agent, or Firm* — Lowenstein Sandler LLP

(57) ABSTRACT

An ambient monitoring device includes a housing, contactless sensors coupled to the housing, and a processing device disposed in the housing. The processing device is coupled to the contactless sensors. The processing device is to receive, from one or more contactless sensors of the plurality of contactless sensors, historical sensor data. The processing device is further to determine baseline vital signs based on the historical sensor data. The processing device is further to receive, from the one or more contactless sensors, current sensor data associated with a user that is within a threshold distance of the ambient monitoring device without contacting the ambient monitoring device. The processing device is further to determine, based on the current sensor data, current vital signs of the user. Responsive to determining the current vital signs do not meet the baseline vital signs, the processing device is to provide an alert.

9 Claims, 9 Drawing Sheets

(52) U.S. Cl.
CPC .......... *A61B 5/4875* (2013.01); *A61B 5/7264* (2013.01); *A61B 5/7275* (2013.01); *A61B 5/7405* (2013.01); *A61B 5/746* (2013.01); *A61B 2562/0219* (2013.01); *A61B 2562/0271* (2013.01); *A61B 2562/029* (2013.01)

(58) Field of Classification Search
CPC ....... A61B 5/0008; A61B 5/0022; A61B 5/01; A61B 5/015; A61B 5/1117; A61B 5/1455; A61B 5/6804; A61B 5/6806; A61B 5/6807; A61B 5/6817; A61B 2560/0475; A61B 2562/0271
USPC ........................................................ 382/128
See application file for complete search history.

(56) References Cited

U.S. PATENT DOCUMENTS

| | | | |
|---|---|---|---|
| 9,568,595 B2 | 2/2017 | Zack et al. | |
| 9,576,468 B2 | 2/2017 | Zack et al. | |
| 10,037,671 B2 | 7/2018 | Zack et al. | |
| 10,276,018 B2 | 4/2019 | Brillaud | |
| 10,410,498 B2 | 9/2019 | Coke et al. | |
| 10,762,990 B1* | 9/2020 | Schilling | G16B 40/30 |
| 2015/0057557 A1* | 2/2015 | Howie | G16Z 99/00 |
| | | | 600/509 |
| 2015/0164375 A1 | 6/2015 | Schindhelm et al. | |
| 2015/0164437 A1* | 6/2015 | McCombie | A61B 5/1117 |
| | | | 600/301 |
| 2019/0057777 A1 | 2/2019 | Joshi et al. | |
| 2019/0108913 A1 | 4/2019 | Coke et al. | |
| 2019/0287376 A1 | 9/2019 | Netscher et al. | |
| 2020/0004247 A1* | 1/2020 | Jacobsen | G05D 1/0221 |

OTHER PUBLICATIONS

"Aloe Care Health", URL: http://www.get.aloecare.com, retrieved on May 18, 2022, 8 pages.

"Vayyar Care", URL: http://www.vayyar.com/care/b2b, retrieved on May 18, 2022, 8 pages.

"Tellus", URL: http://www.tellusyoucare.com, retrieved on May 18, 2022, 7 pages.

"Koko", URL: http://www.fullsleep.com, retrieved on May 18, 2022, 3 pages.

"Xandar Kardian", URL: http://www.kardian.com, retrieved on May 18, 2022, 16 pages.

"binah.ai", URL: http://www.binah.ai/vital-signs, retrieved on May 18, 2022, 12 pages.

"Domalys", URL: http://www.domalys.com/en/detecteur-chute-ehpad, retrieved on May 18, 2022, 1 page.

"SafelyYou", URL: http://www.safely-you.com/how-it-works, retrieved on May 18, 2022, 11 pages.

"Echocare Technologies", URL: http://www.echocare-tech.com/solution-.html, retrieved on May 18, 2022, 3 pages.

"Cherry Home", URL: http://get.cherryhome.ai/care, retrieved on May 18, 2022, 12 pages.

* cited by examiner $$\omega = \frac{2\pi \Delta d}{\lambda}$$

CONTACTLESS SENSOR-DRIVEN DEVICE, SYSTEM, AND METHOD ENABLING AMBIENT HEALTH MONITORING AND PREDICTIVE ASSESSMENT

RELATED APPLICATIONS

This application claims the benefit of U.S. Provisional App. No. 63/007,983, filed Apr. 10, 2020, and U.S. Provisional App. No. 63/119,015, filed Nov. 30, 2020, the entire contents of which are incorporated by reference.

BACKGROUND

While data is used to analyze and understand many aspects of our lifestyle and routines on a daily basis, assessing an individual's health primarily still requires a trip to a doctor's office, and the detection and treatment of health issues is almost always reactive.

BRIEF DESCRIPTION OF DRAWINGS

The examples described herein will be understood more fully from the detailed description given below and from the accompanying drawings, which, however, should not be taken to limit the application to the specific examples, but are for explanation and understanding only.

DETAILED DESCRIPTION

Figure 1:
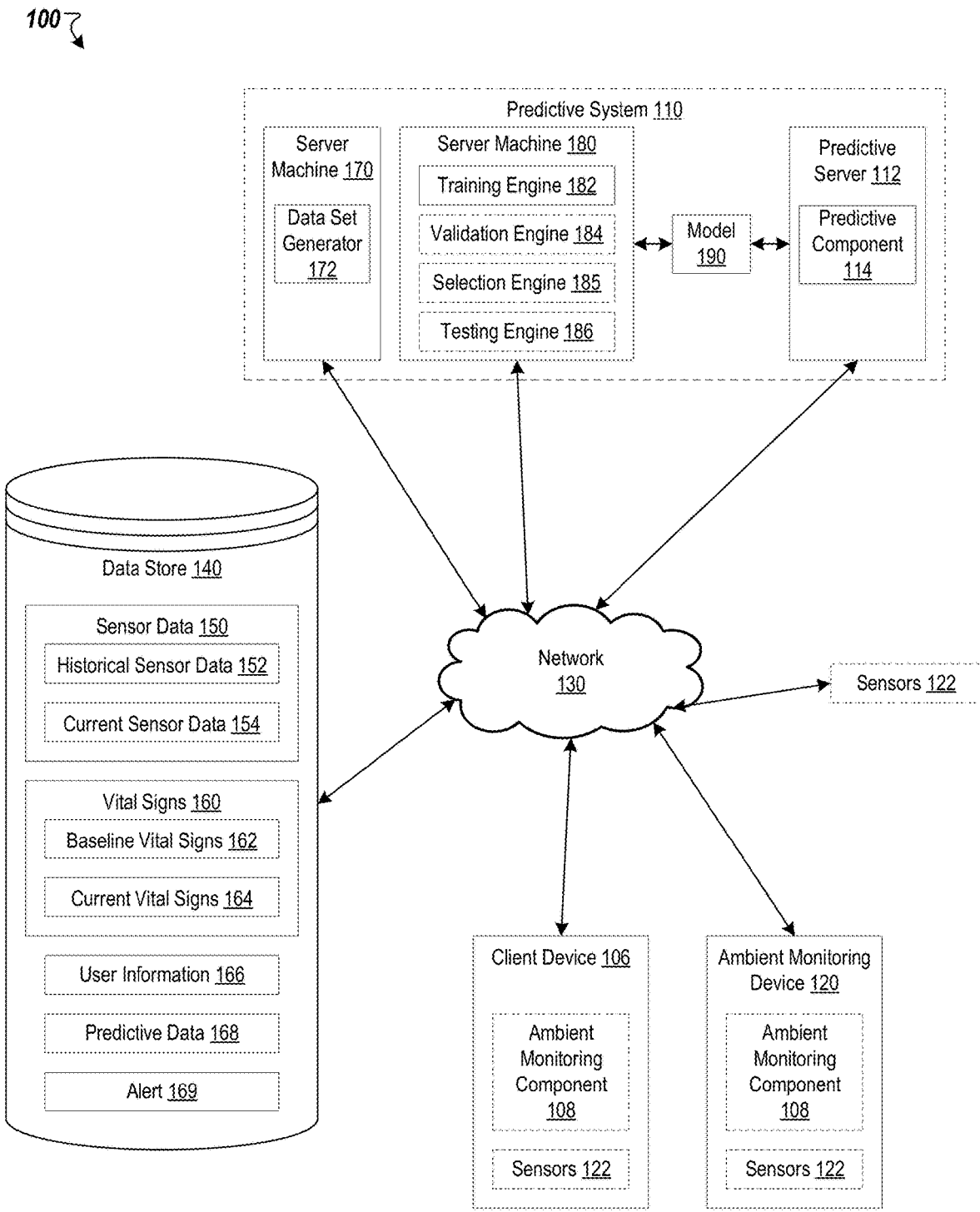
FIG. 1 is a block diagram illustrating an exemplary system architecture, according to certain embodiments.

Embodiments described herein are related to a contactless sensor-driven device, system, and method (e.g., enabling ambient health monitoring, predictive assessment, assessment of arterial stiffness, etc.).

Conventionally, assessing health of a user is at a medical facility (e.g., a trip to the doctor's office) and health assessment is reactive.

Conventional solutions for monitoring the health condition or activity of an individual in a non-healthcare setting typically include wearable or contact-enabled devices. Unfortunately, there are limitations associated with these solutions, such as forgetting to wear a device, the need to charge a wearable device, and difficulty in incorporating reliable sensor technology just to name a few. Although there are also non-wearable solutions in the market, many are intrusive (e.g., requiring multiple cameras to be particularly positioned throughout a monitored space), are limited in their monitoring range, and fail to provide effective preemptive monitoring of health events.

Accordingly, there is a need for an improved solution focused on preventive monitoring of an individual in a non-healthcare setting in order to detect, predict and address health events before they progress or occur all together.

Blood pressure is a well-known indicator in the assessment of cardiovascular health. Although blood pressure is often measured during routine examination of patients, regular and periodic measurement of blood pressure correlating a measurement of arterial stiffness is desirable for better assessing the likelihood of an adverse cardiovascular event.

Using pulse wave velocity (PWV), a reliable measure of arterial stiffness can be determined. PWV is the rate at which a pulse moves (i.e., speed of propagation of a pulse wave) through a blood vessel and, in turn, through the rest of the circulatory system. PWV is determined by measuring a pulse wave between two points in the vasculature—e.g., at a femoral artery and at a jugular artery or, alternatively, at a wrist and at a jugular artery. To measure PWV, a phase and a distance needs to be determined based on the pulse wave detected at the two locations. The phase represents a time difference between pulse waves detected at the two locations, while the distance represents a difference between the distances of the two locations from the heart. Once determined, the distance is divided by the phase to yield the speed at which the pulse wave, or the blood, circulates through an artery. In a healthy adult, typical values are around 6.5 m/s.

Although PWV provides an effective assessment of arterial stiffness, conventional solutions for implementing PWV are cumbersome (e.g., requiring multiple devices connected to a patient to allow for accurate measurement of the minor time difference between two points of a pulse wave).

Accordingly, there is also a need for an improved solution to assess arterial stiffness using PWV on a regular basis and without the need for invasive devices.

In some embodiments, an ambient monitoring device (AMD) is suitable for deployment in a non-healthcare setting (e.g. home or office). The AMD includes contactless sensors and is configured to measure vital signs and activity of one or more users. Various embodiments of the device, system and methods are disclosed, including low level sensors, analysis algorithms, and predictive and diagnosing capabilities based on a pool of sensor data gathered from a larger community of AMDs.

The devices, systems, and methods disclosed herein provide contactless sensor-driven device, system, and method (e.g., enabling ambient health monitoring, predictive assessment, assessment of arterial stiffness, etc.). In some embodiments, the present disclosure uses contactless sensors to monitor and respond to detected events that relate to the well-being of an individual. In some embodiments, the present disclosure relates generally to assessing cardiovascular health and may include to a non-invasive device, system and method of assessing arterial stiffness using one or more contactless sensors. In some embodiments, the present disclosure addresses the shortcomings of existing solutions by providing an improved device, system and method for measuring pulse waves to calculate PWV and, in turn, yield an assessment of arterial stiffness.

In some embodiments, an ambient monitoring device (e.g., monitoring device) including a plurality of contactless sensors is provided (e.g., to measure vital signs and assess activity of an individual in their ambient surroundings). The ambient monitoring device (e.g., using the contactless sensors) may be configured to detect, measure, monitor and provide alerts, where appropriate, in connection with various vital signs, movement, recognized routines, and activity of an individual. This may include, but not limited to, heart rate (including HRV), breathing rate (including BRV), temperature, sleep quality, falls (detected or determined to be imminent), PWV, and various activity/routines. Data collected by contactless sensors may be processed in accordance with various algorithmic processes, as described herein. These algorithmic processes may be executed directly on the ambient monitoring device, remote from the ambient monitoring device, or a combination of both.

In the context of calculating PWV, one or more sensors may be deployed to determine the proximity of a subject, measure phase differences of detected pulse waves in the subject, and measure distance between pulse wave acquisitions in the subject. Data collected by sensors may be processed in accordance with various algorithmic processes suited for measurement of PWV. These algorithmic processes may be executed directly on the monitoring device, remote from the monitoring device or, in some instances, a combination of both. Additionally, the foregoing sensors may be integrated in a single monitoring device unit, coupled to a centralized monitoring device, or any suitable combination thereof depending on the monitoring environment.

The ambient monitoring device may be integrated as part of an overall health monitoring system, whereby the system may be comprised of the ambient monitoring device, a plurality of mobile devices associated with various individuals (e.g., patients, health care providers, family members, etc.) configured with monitoring/notifying applications (e.g., a caregiver application), one or more servers, one or more databases, and one or more secondary systems that are communicatively coupled to enable the health monitoring system of the present disclosure.

An ambient monitoring device includes a housing, contactless sensors coupled to the housing, and a processing device disposed in the housing. In some embodiments, the housing is configured to be placed on a substantially horizontal surface (e.g., on the floor, on a table, on a counter, etc.). In some embodiments, the housing is configured to be secured to a substantially horizontal surface (e.g., ceiling, floor, table, counter, etc.). In some embodiments, the housing is configured to be attached to a substantially vertical surface (e.g., to a wall).

The contactless sensors may provide sensor data associated with a user that is a threshold distance from the contactless sensors without the user contacting the contactless sensors (e.g., and without the user contacting the ambient monitoring device.

In some embodiments, one or more contactless sensors are disposed in an interior volume formed by the housing. In some embodiments, one or more contactless sensors are attached to a surface of the housing (e.g., inside surface, outer surface, etc.). In some embodiments, one or more contactless sensors are remote from the housing and communicate with the processing device disposed in the housing.

The processing device receives, from one or more contactless sensors of the ambient monitoring device, historical sensor data and determines, based on the historical sensor data, baseline vital signs. The processing device receives, from contactless sensors of the ambient monitoring device, current sensor data associated with a user (e.g., that is within a threshold distance of the ambient monitoring device without contacting the ambient monitoring device) and determines, based on the current sensor data, current vital signs of the user. Responsive to determining the current vital signs do not meet the baseline vital signs, the processing device provides an alert.

The devices, systems, and methods of the present disclosure have advantages over conventional solutions. The present disclosure can be used in a location (e.g., home, office, store, restaurant, etc.) that is not a medical facility to determine health conditions compared to conventional solutions of visiting a medical facility to determine health conditions. The present disclosure can be used to predict and prevent health conditions compared to conventional solutions that are reactive. The present disclosure can be contactless compared to conventional wearable solutions that users forget to wear, users forget to charge, and are limited in incorporation of components in the conventional wearable device. The present disclosure may be a single non-intrusive device that has ease of installation compared to intrusive conventional solutions of multiple cameras particularly positioned throughout an indoor space that have a more difficult installation. The present disclosure is non-invasive compared to invasive conventional solutions that include multiple devices connected to a user over time.

Although some embodiments of the present disclosure refer to an ambient monitoring device that includes contactless sensors and a processing device disposed in and/or coupled to a housing, in some embodiments, one or more components of the ambient monitoring device may be disposed remote from the housing.

FIG. 1 is a block diagram illustrating an exemplary system architecture of system 100, according to certain embodiments. The system 100 includes a client device 106, ambient monitoring device 120, sensors 122, a predictive server 112, and a data store 140. The predictive server 112 may be part of a predictive system 110. The predictive system 110 may further include server machines 170 and 180.

Ambient monitoring device 120 includes a housing and processing device (e.g., controller, processing device 802 of FIG. 8) disposed in the housing. The ambient monitoring device 120 may include an ambient monitoring component 108 (e.g., executed by the processing device).

In some embodiments, client device 106 includes a computing device such as a personal computer (PC), desktop computer, laptop, mobile phone, smart phone, tablet computer, netbook computer, etc. Client device 106 includes a housing and processing device (e.g., controller, processing device 802 of FIG. 8) disposed in the housing. The client device 106 may include an ambient monitoring component 108 (e.g., executed by the processing device).

Ambient monitoring component 108 may receive user input. The user input may be received via a user interface (e.g., graphical user interface (GUI), button, knob, etc.) of the ambient monitoring device 120 or client device 106. In some embodiments, the ambient monitoring component 108 transmits data (e.g., sensor data 150, vital signs 160, user information 166, etc.) to the predictive system 110, receives output (e.g., predictive data 168) from the predictive system 110, determines a corrective action (e.g., alert 169) based on the output, and causes the corrective action to be implemented (e.g., provides the alert 169). Client device 106 and ambient monitoring device 120 may include an operating system that allows users to one or more of generate, view, or edit data.

Sensors 122 may be contactless sensors. Sensors 122 may be coupled to (e.g., disposed in housing of, coupled to housing of) ambient monitoring device 120 and/or client device 106. One or more sensors 122 may be remote from the ambient monitoring device 120 and/or client device 106. Sensors 122 may include one or more of a high-resolution visible light camera, an infrared imaging sensor, a motion radar imaging sensor, a microphone array sensor, a vibration sensor, accelerometer sensor, a depth sensor, ambient temperature sensor, or ambient humidity sensor. Sensors 122 may provide sensor data 150.

Ambient monitoring component 108 and/or predictive component 114 may determine one or more vital signs 160 based on sensor data 150. Ambient monitoring component 108 and/or predictive component 114 may combine sensor data 150 from one or more sensors 122 (e.g., to form structured data) to determine vital signs 160. Ambient monitoring component 108 and/or predictive component 114 may determine vital signs 160 based on sensor data 150 and user information 166.

The client device 106, ambient monitoring device 120, sensors 122, predictive server 112, data store 140, server machine 170, and server machine 180 may be coupled to each other via a network 130 for determining predictive data 168 to perform corrective actions. In some embodiments, network 130 is a public network that provides client device 106 and/or ambient monitoring device 120 with access to the predictive server 112, data store 140, and other publically available computing devices. In some embodiments, network 130 is a private network that provides access to the data store 140 and other privately available computing devices and that provides client device 106 and/or ambient monitoring device 120 access to the predictive server 112, data store 140, and other privately available computing devices. Network 130 may include one or more wide area networks (WANs), local area networks (LANs), wired networks (e.g., Ethernet network), wireless networks (e.g., an 802.11 network or a Wi-Fi network), cellular networks (e.g., a Long Term Evolution (LTE) network), routers, hubs, switches, server computers, cloud computing networks, and/or a combination thereof.

The predictive server 112, server machine 170, and server machine 180 may each include one or more computing devices such as a rackmount server, a router computer, a server computer, a PC, a mainframe computer, a laptop computer, a tablet computer, a desktop computer, graphics processing unit (GPU), accelerator application-specific integrated circuit (ASIC) (e.g., tensor processing unit (TPU)), etc.

The predictive server 112 may include a predictive component 114. In some embodiments, the predictive component 114 may retrieve current data (e.g., current sensor data 154, etc.) from the data store and generate output (e.g., predictive data 168) for performing a corrective action (e.g., providing an alert). In some embodiments, the predictive component 114 may use a model 190 (e.g., polynomial fit, empirical model, trained machine learning model, etc.) to determine the output for performing the corrective action. The model 190 may be trained using historical data (e.g., historical sensor data 152, baseline vital signs 162, etc.) to learn key parameters. In some embodiments, the predictive component 114 determines predictive data 168 for performing corrective action by providing current data (e.g., current sensor data 154, etc.) into the trained model 190, obtaining output from the trained model 190, and determining predictive data 168 based on the output.

Data store 140 may be memory (e.g., random access memory), a drive (e.g., a hard drive, a flash drive), a database system, or another type of component or device capable of storing data. Data store 140 may include multiple storage components (e.g., multiple drives or multiple databases) that may span multiple computing devices (e.g., multiple server computers). The data store 140 may store sensor data 150, vital signs 160, user information 166, predictive data 168, alerts 169, and/or the like. The sensor data 150 may include historical sensor data 152 and current sensor data 154. The vital signs 160 may include baseline vital signs 162 and the current vital signs 164. Historical data may be data (e.g., historical sensor data 152, baseline vital signs 162, etc.) that is used to train a model 190. Current data may be data (e.g., current sensor data 154, current vital signs 164, etc.) used to generate predictive data 168 and/or used to re-train model 190.

Each instance (e.g., set) of sensor data 150, vital signs 160, user information 166, predictive data 168, and/or alert 169 may correspond to a respective user and/or a corresponding period of time.

Sensor data 150 may be data (e.g., a combination of data, processed data, etc.) from one or more sensors 122. Sensor data 150 may include one or more of images, visible light data, infrared data, motion radar data, microphone data, vibration data, accelerometer data, depth data, ambient temperature data, ambient humidity data, and/or the like. Sensor data 150 may be associated with one or more users (e.g., people within a threshold distance of sensors 122). Different sets of sensor data 150 may be associated with a corresponding user identifier (e.g., a first set of sensor data 150 is associated with a first user and a second set of sensor data 150 is associated with a second user).

Vital signs 160 may be derived in part from sensor data 150 and/or user information 166. Vital signs 160 may be indicative of a health condition (e.g., current health condition, future health condition, predictive health condition, etc.) of a user. Vital signs 160 may include one or more of heart rate, breathing rate, body temperature, body movement, body position, user activity in ambient surroundings, hydration, blood pressure, and/or changes in skin color tone. In some embodiments, baseline vital signs 162 are based on sensor data 150 from multiple people. In some embodiments, baseline vital signs 162 and current vital signs 164 are specific to one user. In some embodiments, baseline vital signs 162 includes a threshold range of vital sign data (e.g., an acceptable range of temperatures, an acceptable range of heart rate, etc.).

User information 166 may be received via user input via client device 106 and/or ambient monitoring device 120. User information may be indicative of a health condition of a user.

Predictive data 168 may be generated by predictive component 114 based on current sensor data 154. Predictive data 168 may be a prediction of current vital signs 164 based on current sensor data 154.

Alert 169 may be generated by ambient monitoring component 108 based on the predictive data 168 and/or current vital signs 164. The alert 169 may be provided via ambient monitoring device 120 and/or client device 106 (e.g., client device 106 of the user associated with the alert 169, client device 106 of a user remote from the user associated with the alert 169, client device of a health care provide of the user associated with the alert 169, etc.). The alert 169 may be indicative of current vital signs 164 that do not meet baseline vital signs 162 (e.g., are not within a threshold value of baseline vital signs 162). The alert 169 may be indicative of predictive vital signs that may not meet of baseline vital signs 162 (e.g., are not within a threshold value of baseline vital signs 162). The alert 169 may be indicative of a poor health condition or a predictive poor health condition.

In some embodiments, the client device 106 and/or ambient monitoring device 120 may store historical data and/or current data in the data store 140 and the predictive server 112 may retrieve the historical data and/or current data from the data store 140. In some embodiments, the predictive server 112 may store output (e.g., predictive data 168) of the trained model 190 in the data store 140 and the client device 106 and/or ambient monitoring device 120 may retrieve the output from the data store 140.

In some embodiments, predictive system 110 further includes server machine 170 and server machine 180. Server machine 170 includes a data set generator 172 that is capable of generating data sets (e.g., a set of data inputs, a set of data inputs and a set of target outputs) to train, validate, and/or test a model 190. Some operations of data set generator 172 are described in detail below with respect to FIGS. 6A and 7A. In some embodiments, the data set generator 172 may partition the historical data into a training set (e.g., sixty percent of the historical data), a validating set (e.g., twenty percent of the historical data), and a testing set (e.g., twenty percent of the historical data). In some embodiments, the predictive system 110 (e.g., via predictive component 114) generates multiple sets of features (e.g., based on combinations of sensor data 150, etc.).

Server machine 180 includes a training engine 182, a validation engine 184, selection engine, and/or a testing engine 186. An engine (e.g., training engine 182, a validation engine 184, selection engine 185, and a testing engine 186) may refer to hardware (e.g., circuitry, dedicated logic, programmable logic, microcode, processing device, etc.), software (such as instructions run on a processing device, a general purpose computer system, or a dedicated machine), firmware, microcode, or a combination thereof. The training engine 182 may be capable of training a model 190 using one or more sets of features associated with the training set from data set generator 172. The training engine 182 may generate multiple trained models 190, where each trained model 190 corresponds to a distinct set of features of the training set (e.g., sensor data from a distinct set of sensors). For example, a first trained model may have been trained using all features (e.g., X1-X5), a second trained model may have been trained using a first subset of the features (e.g., X1, X2, X4), and a third trained model may have been trained using a second subset of the features (e.g., X1, X3, X4, and X5) that may partially overlap the first subset of features.

The validation engine 184 may be capable of validating a trained model 190 using a corresponding set of features of the validation set from data set generator 172. For example, a first trained model 190 that was trained using a first set of features of the training set may be validated using the first set of features of the validation set. The validation engine 184 may determine an accuracy of each of the trained models 190 based on the corresponding sets of features of the validation set. The validation engine 184 may discard trained models 190 that have an accuracy that does not meet a threshold accuracy. In some embodiments, the selection engine 185 may be capable of selecting one or more trained models 190 that have an accuracy that meets a threshold accuracy. In some embodiments, the selection engine 185 may be capable of selecting the trained model 190 that has the highest accuracy of the trained models 190.

The testing engine 186 may be capable of testing a trained model 190 using a corresponding set of features of a testing set from data set generator 172. For example, a first trained model 190 that was trained using a first set of features of the training set may be tested using the first set of features of the testing set. The testing engine 186 may determine a trained model 190 that has the highest accuracy of all of the trained models based on the testing sets.

The model 190 may refer to the model artifact that is created by the training engine 182 using a training set that includes data inputs and, in some embodiments, corresponding target outputs (correct answers for respective training inputs). Patterns in the data sets can be found that cluster the data input and/or map the data input to the target output (the correct answer), and the model 190 is provided mappings that captures these patterns. The model 190 may use one or more of machine learning model, polynomial fit, empirical model, unsupervised machine learning model, supervised machine learning model, linear regression, random forest, neural network (e.g., artificial neural network), etc.

Predictive component 114 may provide current data (e.g., current sensor data 154 and current vital signs 164) to the trained model 190 and may run the trained model 190 on the input to obtain one or more outputs. The predictive component 114 may be capable of determining (e.g., extracting) predictive data 168 from the output of the trained model 190 and may determine (e.g., extract) confidence data from the output that indicates a level of confidence that the predictive data 168 corresponds to the current sensor data 154 (e.g., predictive data 168 matches current vital signs 164 of the user). The predictive component 114 or ambient monitoring component 108 may use the confidence data to decide whether to cause a corrective action (e.g., provide an alert) based on the predictive data 168.

The confidence data may include or indicate a level of confidence that the predictive data 168 corresponds to the current vital signs 164. In one example, the level of confidence is a real number between 0 and 1 inclusive, where 0 indicates no confidence that the predictive data 168 corresponds to the current vital signs 164 and 1 indicates absolute confidence that the predictive data 168 corresponds to the current vital signs 164. In some embodiments, the system 100 may use predictive system 110 to determine predictive data 168 instead of determining current vital signs 164 as often, etc. In some embodiments, responsive to the confidence data indicating a level of confidence that is below a threshold level, the system 100 may determine the current vital signs 164 (e.g., via ambient monitoring component 108 and/or client device 106, via user input, etc.). Responsive to the confidence data indicating a level of confidence below a threshold level for a predetermined number of instances (e.g., percentage of instances, frequency of instances, total number of instances, etc.) the predictive component 114 may cause the trained model 190 to be re-trained (e.g., based on the current data 164, etc.).

For purpose of illustration, rather than limitation, aspects of the disclosure describe the training of a model using historical data and inputting current data 164 into the trained model to determine predictive data 168. In other implementations, a heuristic model or rule-based model is used to determine predictive data 168 (e.g., without using a trained model). Predictive component 114 may monitor historical data. Any of the information described with respect to data inputs 601 of FIG. 6A may be monitored or otherwise used in the heuristic or rule-based model.

In some embodiments, the functions of client device 106, ambient monitoring device 120, predictive server 112, server machine 170, and server machine 180 may be provided by a fewer number of machines. For example, in some embodiments server machines 170 and 180 may be integrated into a single machine, while in some other embodiments, server machine 170, server machine 180, and predictive server 112 may be integrated into a single machine. In some embodiments, two or more of client device 106, ambient monitoring device 120, and/or predictive server 112 may be integrated into a single machine.

In general, functions described in one embodiment as being performed by client device 106, ambient monitoring device 120, predictive server 112, server machine 170, and server machine 180 can also be performed on predictive server 112 in other embodiments, if appropriate. In addition, the functionality attributed to a particular component can be performed by different or multiple components operating together. For example, in some embodiments, the predictive server 112 may determine the corrective action (e.g., alert 169) based on the predictive data. In another example, client device 106 and/or ambient monitoring device 120 may determine the predictive data 168 based on output from the trained model.

In addition, the functions of a particular component can be performed by different or multiple components operating together. One or more of the predictive server 112, server machine 170, or server machine 180 may be accessed as a service provided to other systems or devices through appropriate application programming interfaces (API).

In embodiments, a "user" may be represented as a single individual. However, other embodiments of the disclosure encompass a "user" being an entity controlled by a plurality of users and/or an automated source. For example, a set of individual users federated as a group of administrators may be considered a "user."

Although embodiments of the disclosure are discussed in terms of generating predictive data 168 to perform a corrective action (e.g., provide an alert 169) associated with a user, embodiments may also be generally applied to predicting data to perform an action. For example, data may be collected for predicting future actions.

Figure 2:
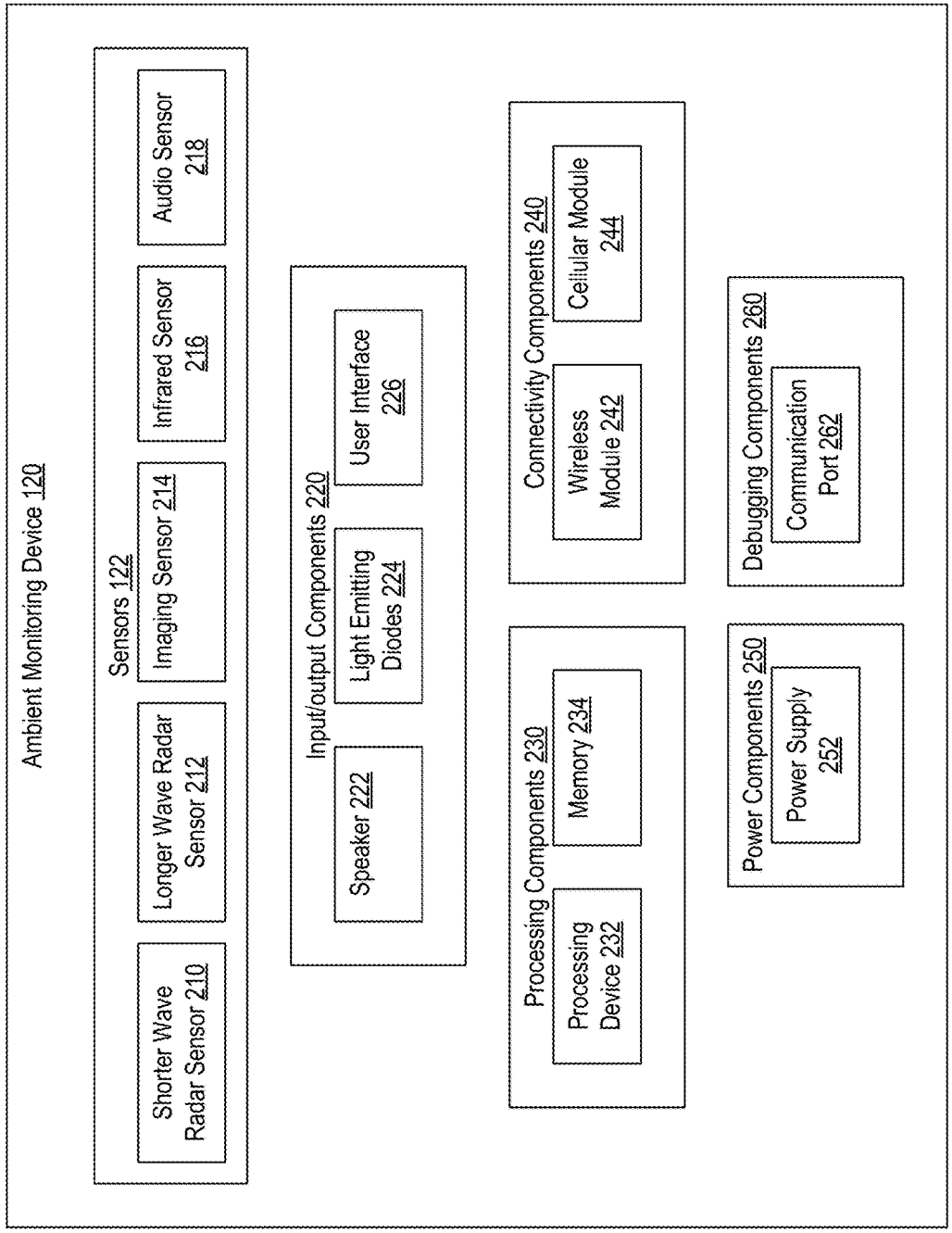
FIG. 2 is a block diagram of an ambient monitoring device, according to certain embodiments.

FIG. 2 is a block diagram of an ambient monitoring device 120, according to certain embodiments.

Ambient monitoring device 120 includes one or more of sensors 122, input/output components 220, processing components 230, connectivity components 240, power components 250, and/or debugging components 260.

Sensors 122 may be contactless sensors (e.g., determine sensor data of a user within a threshold distance without the user contacting the sensor and/or the ambient monitoring device 120). Sensors 122 may include one or more of shorter wave radar sensors 210, longer wave radar sensors 212, imaging sensor 214 (e.g., low resolution image sensor), infrared (IR) sensor 216, audio sensor 218 (microphone array sensor), and/or the like.

Shorter wave radar sensors 210 may be one or more of a millimeter-wave (mmWave) radar integrated circuit (IC), may have an antenna in a package, may be used to determine heart rate, used to determine breathing rate, is short range, is about 60 gigahertz (GHz), and/or may be forward facing.

Longer wave radar sensors 212 may be one or more of centimeter-wave (cmWave) radar IC, point cloud (three dimensional (3D)) long range, orientation detection, fall detection, activity detection, multiple person detection, raw data output available, 180 or 360 degree, and/or the like. The longer wave radar sensors 212 may include an antenna array include one or more of transmitter (Tx) and receiver (Rx), 6 to 10 GHz, forward array, and/or rear array.

The imaging sensor 214 may include one or more of face and/or person detection, temperature detection, and/or may correlate to radar data (e.g., from shorter wave radar sensor 210 and/or longer wave radar sensor 212).

The infrared sensor 216 may one or more of provide a temperature profile (e.g., of the ambient array, of a user, etc.) and/or may be radiometric.

The audio sensor 218 may one or more of be a microphone array, be in communication with the user, be high quality, and/or be medium to long range.

Input/output components 220 may include one or more of speaker 222 (e.g., audio component), light emitting diodes 224 (LEDs), user interface 226 (e.g., general purpose input/output interface, user input interface), and/or the like. The speaker 222 may be one or more of 2 to 4 watts, class D amp, long to medium range, and/or have volume control. The LEDs 224 may one or more of provide a visual indication to the user and/or be a red-green-blue (RGB) light pipe. The user interface 226 may be one or more of a power on/off interface, device reset interface, and/or push buttons interface.

Processing components 230 may include a processing device 232 (e.g., application processor, processing device 802 of FIG. 8) and/or memory 234. The processing device 232 may be one or more of Linux, CPU, GPU, digital signal processor (DSP), and/or artificial intelligence engine (e.g., model 190 of FIG. 1). In some embodiments, the memory 234 is a DDR.

Connectivity components 240 may include a wireless module 242 and/or a cellular module 244. The wireless module 242 may include one or more of WiFi, BLE, and/or Sub 1 Ghz. The wireless module 242 may provide one or more of 802.11 a/g/c/n, AP mode, act as a hub, and/or the like. The cellular module 244 may one or more of an LTE module, a full-duplex, VoLTE, 3G/2G fallback, and/or global coverage. The connectivity components 240 may further include one or more of MIMO 2.4 GHz antennas, Sub 1 GHz antenna, wideband antenna, diversity antenna, SIM, eSIM, and/or the like.

Power components 250 may include a power supply 252. The power supply 252 may be one or more of external, low noise, USB-C or barrel jack, 5 Volts (V), 12 V, 24 V, medical or ITE, rechargeable battery, replaceable battery, wiring to an external power supply, and/or the like.

Debugging components 260 may include a communications port 262. The communications port may one or more of provide a functional test, provide firmware upgrade, be used for debugging, and/or the like.

A plurality of sensors 122 may be deployed in the ambient monitoring device 120. In some embodiments, sensors 122 include a high resolution visible light camera having a minimum resolution of 720p and frame rate of 30 fps (preferably 60 fps). In some embodiments, sensors 122 include an infrared imaging sensor having a minimum resolution of 32 pixels to 128 pixels wide (LWIR), and further enabled with radiometric and normalized sensing. In some embodiments, sensors 122 include one or more 3D and motion radar imaging sensors using FMW or impulse radar technology at a short range. A first radar sensor may be configured to function in the 60 GHz-100 GHz band to provide high resolution images, but is not suited to penetrate typical home obstacles/barriers, such as walls or furniture (the "millimeter (mm) wave" radar—also referred to herein as "mmWave"). A second radar sensor may be configured to function in the 6-10 GHz band and is suited to penetrate most home obstacles/barriers at a range of about 10 m (the "centimeter (cm) wave" radar—also referred to herein as "cmWave"). Both radar imaging sensors output the raw FMCW or time of flight data and return phase. Both radar imaging sensors may also have onboard DSP to perform all the FMCW or pulse radar signal processing.

In some embodiments, the ambient monitoring device 120 may be further equipped with one or more of the following additional sensors 122: one or more microphone array sensors with a minimum of 4 arrays; one or more vibration/accelerometer sensors; one or more camera or depth sensors; and/or one or more room temperature and humidity sensors.

In some embodiments, all of the foregoing sensors 122 are connected to an onboard computer unit (e.g., processing device 232 of FIG. 2, processing device 802 of FIG. 8) that will do most of the signal and image processing on the ambient monitoring device 120.

In some embodiments, the ambient monitoring device 120 uses data signals and/or user identification. A plurality of data signals may be collected directly from a user. In some embodiments, the following data signals may be detected and measured by sensors 122 in the ambient monitoring device 120 when a user is in close physical proximity (e.g., less than 2-3 meters) or in direct line of sight to the ambient monitoring device 120:

Heart rate and waveform;
Breathing rate and waveform;
Body temperature and variations; and/or
Color tones of skin on the face versus lip color (e.g., changes in skin color tone).

When an individual is in close audible proximity to the ambient monitoring device 120, the following data signals may be measured:

Sneezing;
Coughing and type of cough; and/or
Loud or irregular breathing.

When an individual is generally in a detectable range of the ambient monitoring device 120, the following data signals may be measured:

Body movement and position; and/or
Falls and type of fall (e.g., impact, distance, etc.).

When an individual is asleep in a detectable range of the ambient monitoring device 120, the following data signals may be measured:

Sleep phases;
Breathing variability; and/or
Apnea detection.

In some embodiments, a plurality of data signals may be collected indirectly from a user. These types of data signals may be derived based on measurements received at sensors 122 of the ambient monitoring device 120. For example, hydration levels may be computed based on detected infrared patterns, blood pressure may be computed based on detected heart waveforms, and core body temperature may be computed based on detected surface temperature and heart rate.

In some embodiments, data collected via sensors 122 may be used to automatically recognize and identify users who revolve around the ambient monitoring device 120 on a regular basis. For example, the following may be used, independently or in various combinations thereof, to form unique identifiers: (i) a camera sensor for facial recognition; (ii) an IR sensor for facial vessel pattern recognition; (iii) heart rate and blood pressure waveforms; (iv) radar sensors as a biometric signal (e.g., human body reflects radar waves in a unique pattern); and (v) audio sensors for voice recognition.

Vital signs data (e.g., vital signs 160) may be associated with a user to track health of the user over time and potentially over several locations. In some embodiments, a primary (personal) ambient monitoring device 120 may be located in the home or office of a user, wherein the primary ambient monitoring device 120 is monitoring the user on a regular basis. However, in some embodiments, one or more sensors 122 of a secondary ambient monitoring device 120 (e.g., in a public space or in a location different than the primary ambient monitoring device 120 location) may collect data for a user and be configured to transmit that data to a centralized identity database (e.g., data store 140). The combination of vital sign and movement data (e.g., sensor data 150, vital signs 160) may be used by the centralized identify database to identify the user and associate the data with the primary ambient monitoring device 120 of the user.

The ambient monitoring device 120 (e.g., via ambient monitoring component 108 of FIG. 1, processing device 232 of FIG. 2, processing device 802 of FIG. 8, and/or the like) may use one or more algorithms. A plurality of algorithms processes may be executed in connection with the ambient monitoring device 120. These algorithmic processes, as described herein, may be used to produce structured data (e.g., vital signs 160) from the raw input (e.g., sensor data 150) of the sensors 122 of ambient monitoring device 120 to detect notable deviations.

The ambient monitoring device 120 (e.g., via ambient monitoring component 108 of FIG. 1, processing device 232 of FIG. 2, processing device 802 of FIG. 8, and/or the like) may generate a map (e.g., mapping) from sensor data 150 (e.g., frequency-modulated continuous wave (FMCW) data, pulse radar data, etc.). The map may be a time-three-dimensional (3D) (four-dimensional (4D)) map of radar reflections using the basic output of an array of various Tx/Rx pairs implementing FMCW principles or impulse radar output. For background, see Introduction to mmwave Sensing: FMCW Radars by Sandeep Rao (https://training.ti-.com/sites/default/files/docs/mmwaveSensing-FMCW-offlineviewing_4.pdf).

The setup configuration utilizes n transmitters and m(n) receivers per transmitter, where n is greater than 1 and m(n) is greater than 2. In one embodiment, there may be up to 3 transmitters and 12-16 receivers used. Three panels are disposed in a triangular fashion to cover 360 degrees, where each panel has roughly a 160 degree angle of vision. Therefore, the three panels arranged in the triangular pattern cover 360 degrees with some overlap. The output of each antenna pair (n, m(n)) is both the phase and amplitude of the return signal.

Figure 4:
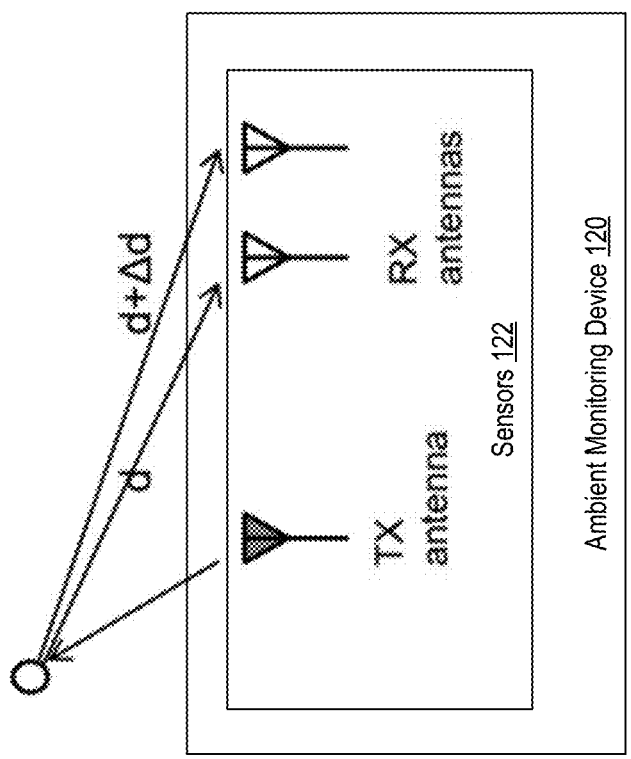
FIG. 4 is a block diagram of an ambient monitoring device, according to certain embodiments.

Angle of arrival (AOA) ($\omega$) of the signal reflected by one object can be detected by two antennas following this schema displayed in FIG. 4 (e.g., based on distance (d) of the antenna (Rx) from the object (O) and the wavelength ($\lambda$) used by the sensor).

Range may be estimated using time of flight. Range variation, as measured by phase changes, results in a Doppler effect and can be used to measure speed of the target.

By looking at phase difference over time and antenna pairs, an estimation of speed and angle of arrival in any point in space can be determined by projecting each of these estimations for each range on each antenna and antenna pair. A 3D Eulerian space may be "painted" with these estimations. The issue is noise (i.e., painting this way creates noise and blurring), but also the fact that the final space is sampled in spherical coordinates. Therefore, spatial sampling for distant points is very low and for closer points is too high.

A new approach is proposed, which comprises a reverse scanning and back projection of these range and AOA estimations—the 3D space is sampled in a Cartesian referential and sampling space. For each voxel of this space, the range for each antenna pair (1RX, 1TX) is computed. For each antenna triplet (1TX, 2RX), the theoretical AOA is computed, hence the phase difference. If one antenna pair has an amplitude peak at the expected range and the right phase difference, this amplitude is assigned to the voxel and its reliability is increased. So for each pixel in this uniformly sampled Cartesian space, we have a confidence score based on how many antenna triplets agree on the hypothesis that there is a radar reflecting piece of material in this voxel, and the intensity of its radar reflection which is relative to its volume and water or metal content. As a result a clean, denoised, uniformly sampled Cartesian volume of the scene is achieved.

For each voxel in this sampled volume, speed or quantity of movement of the corresponding object can be estimated by comparing phase over time. For each TX/RX pair of each TX/RX/RX triplet, phase at a current frame is compared with the next frame, and if the phase varies significantly and the reflected intensity is not too low (meaning there is an object there) then this antenna pair interprets this as movement at this voxel. If several of the pairs taken in all the triplets agree, then movement can be reliably declared in that voxel. This quantity of movement is radial movement.

Each sampling is regular, data is cleaner and signal-to-noise ratio (SNR) is higher. More importantly reflectance index and speed for each voxel is acquired, which is very valuable information to understand human motion. This may be further adapted with highly Cartesian and geometric computations.

Simple signal processing methods may be used to remove static clutter from a radar return signal. This may be performed on range/phase output for each antenna pair, on the final 3D volume, or a combination of both.

In some embodiments, the ambient monitoring device 120 is used for radar speed estimation. The phase of consecutive radar frames for a given antenna pair is compared. As previously described, the phase difference for one antenna pair over time gives an indication of speed per range for this antenna pair. By crossing this information with phase difference, an idea of the gross direction and origin of the movement can be determined (see AOA formula of FIG. 4).

A back sampling approach, as previously described, may be used to evaluate speed for each antenna pair. For simplicity, speed per range as given by one antenna may be used, and this speed is assigned to the largest target in the same range—usually there is only one target per range. This is a very fast and efficient approach.

In some embodiments, the ambient monitoring device 120 is used for radar vital signs sensing. Off the shelf radar algorithms may be used to measure heart rate and breathing rate. These types of algorithms may be provided, for example, on AWR/IWR sensors used in FMCW radars to measure volume variation of the heart and chest.

In some embodiments, the ambient monitoring device 120 is used for visual vital signs sensing. The ambient monitoring device 120 may perform remote photoplethysmography (rPPG) with RGB or Infrared. Heart rate of a user may be measured using an infrared or visible light camera.

Remote photoplethysmography (rPPG) may be used to measure heart rate. Plethysmography (PPG) may be used to measure the presence or absence of blood in vessels—the skin has lots of vessels so it is easy to measure it there. This PPG wave form may then be used to compute heart rate.

An RGB camera is mostly sensitive to the visible light wavelengths range (approximately from 400 to 1000 nm), but also demonstrates some response to the near-infrared wavelengths. Therefore, on a homogenous skin surface, color changes induced by blood flow variations can be measured by such a sensor.

Starting from a live feed of RGB camera, a face detection algorithm is performed in real time. Next, this detection is refined in order to accurately detect stable facial landmarks that are used to extract skin patches. By studying the fine color variations (e.g., at 30/60 fps) in those patches, and making use of signal processing methods, the heart rate and breathing rate of an individual standing in front of the camera may be measured.

In some embodiments, the ambient monitoring device 120 is used for skin temperature measurement with an IR sensor of the ambient monitoring device 120. A long wave infrared (LWIR) sensor is sensitive to the 8000-14000 nm wavelength range, allowing for the temperature at the surface of objects placed in the camera field to be measured.

In order to measure the skin surface temperature, a face detection method (e.g., proprietary face detection algorithm) in the infrared space may be used to measure a skin patch on the forehead of a user. First, the IR space outside of the range of interest (typically, 29-34 degrees C. or 84-93 degrees F.) is discarded, and then an elliptic blob within those thresholds is identified. Skin temperature may be measured when an individual is in close proximity to the infrared sensor (e.g., less than 5 feet away). The accuracy of this method may be cross-checked using a laser thermometer.

In some embodiments, the ambient monitoring device 120 is used to determine hydration and oxygenation levels using IR and RGB. Pattern of vessels in the face seen through an IR sensor change in intensity based on body hydration. These changes can be measured and used to derive changes in hydration levels.

Oxygenation levels have a direct impact on the tone and color of the face. Skin and lips have different variations in color based on oxygenation. RGB color and tone can be measured for each part of the face using a face feature detector, as described above, to spot skin vs lips.

In some embodiments, the ambient monitoring device 120 is used for other visual indications. Other specific patterns can be detected visually, such as the color of white of the eyes, marbling of the skin, etc. These visual characteristics can be attributed to specific conditions and used, for example, in combination with other measured vital signs (described in the following section) to determine or verify a perceived health condition of a user being monitored.

In some embodiments, sensor data 150 from multiple sensors 122 of the ambient monitoring device 120 is combined (e.g., sensor fusion). Data collected from multiple sensors 122 may be used in a collaborative manner to produce enhanced data for more accurately determining the health condition of an individual being monitored.

In some embodiments, the ambient monitoring device 120 performs geometric camera and infrared sensor calibration. Geometric calibration is the process of characterizing the intrinsic parameters of an imaging sensor. The analysis may be performed on both the RGB camera and the IR sensor, in order to then perform the extrinsic calibration between them. The latter characterization provides a bijective function between the fields of our sensors.

In some embodiments, the ambient monitoring device 120 is used for measuring IR skin temperature using camera (e.g., imaging sensor 214 and IR Sensor 216. An accurate face detection is performed in the RGB video, and then skin patches are projected in the infrared field, in order to retrieve the surface temperature. Combining skin temperature with heart rate (measured by rPPG, radar or combination of both as described below) enables accurate prediction of core body temperature.

In some embodiments, the ambient monitoring device 120 is performs rPPG using one or more IR sensors 216 and one or more imaging sensors 214 (e.g., RGB sensor). A physically static patch of skin may also be used in the infrared sensor, as determined by facial feature detection in the RGB camera, then converted into the IR camera to measure the pleth as in rPPG (remote plethysmography), or presence or absence of blood in vessels.

As for temperature measurement, the face is detected in the visible light camera, then fine infrared changes are measured for a static point relative to face features (temples, forehead, neck, etc.) to estimate PPG.

In some embodiments, the ambient monitoring device 120 is used for precise core temperature estimation using heart rate (rPPG or radar) and IR sensor. Surface temperature is a function of core body temperature and temperature transfer through the skin. Temperature transfer is faster if more blood is in the veins and arteries, so temperature transfer is related to heart rate and heart waveform. A statistical model may be trained to infer precise core temperature from precise surface temperature, as described above, and precise heart rate or vascular pleth waveform.

An emissivity coefficient is typically unique for each individual—it can vary based on age, gender and a various combination of other parameters. An individual can be identified using, for example, the camera sensor and corresponding facial recognition algorithms. An emissivity coefficient for the identified individual can be measured and evaluated (assuming the individual has no temperature during the first days of usage of the system—users may be asked to confirm during setup). Using the measured emissivity coefficient, the core body temperature can be evaluated from skin temperature in a very precise manner.

In some embodiments, the ambient monitoring device 120 is used for cmWave and mmWave radar collaboration for fine movement detection. When an individual is in the same room as the monitoring device, movement and position can be measured with both shorter wave and longer wave radars. Both 3d maps may then be combined to have a more stable, more accurate and more robust model of the human body.

In some embodiments, the ambient monitoring device 120 is used for signal understanding and higher level machine learning. In some embodiments, machine learning models may be trained to detect higher level information from sensors 122 and raw vital signs.

In some embodiments, the ambient monitoring device 120 is used for radar-based activity detection. Users be detected from a cm wave radar point cloud using body models.

A machine learning model is trained to recognize human posture and activity from the signal obtained using a high accuracy visual stereoscopic sensor. The sensor is mounted on the ambient monitoring device 120 and, with an individual in line of sight, various positions and movement can be recognized (e.g., sitting, walk, running, etc.).

A high accuracy body structure algorithm, such as open pose, may be run on the stereoscopic sensor output. A machine learning model is then trained that runs on the output of the cm or mm wave radars point clouds to recognize the same structures.

The task may also be simplified to simple positions or movements—standing, sitting, laying down for positions, standing up, sitting down or falling for movements. Those movements are detected on the stereoscopic sensor and a dynamic time model is trained on the radar data to recognize those movements.

Once the model is trained, we infer it on the single radar data (no more stereo vision input) and the radar can see what the visual stereoscopic sensor and open pose stacks could see before. This works through standard structures as the cm wave radar signal can go through walls.

In some embodiments, the ambient monitoring device 120 is used for floor modeling. The range of the radar sensing of the ambient monitoring device 120 may be automatically limited, for example, to one floor and or one apartment. A user may not need to input a floor plan or map. Instead, the ambient monitoring device 120 may determine this simply by observing activity.

Once the ambient monitoring device 120 is active (e.g., turned on), individuals may be observed to detect their lower boundaries and estimate statistically where the floor is. The space may be sampled in 3D and the score increased for "floor" for a voxel if a lower boundary for an individual is detected there. Over time a reliable floor model is established.

In some embodiments, the ambient monitoring device 120 is used for apartment boundaries modeling. A similar approach to floor modeling may be used to infer apartment boundaries. Insight such as sound and video may be used to guess if an individual is at home. When a determination is made that the individual is home, the score of each voxel is increased in the 3D sampling space when we detect an individual is present in an area. Over time, a map of where individuals usually are present is constructed and detection may be focused on those areas. A floor plan may also be inferred.

In some embodiments, the ambient monitoring device 120 is used for data analysis and prediction. The ambient monitoring device 120 is configured to record activity and vital signs over time. The ambient monitoring device 120 is further configured to detect serious events, such as heart issues, respiratory issues and falls.

A large amount of data may be collected for a single user, as well as many users, which may be used to understand and detect individual specific or generic patterns that are precursors to serious health problems. Using a corpus of such data coming from various individuals, a machine learning model can be trained to detect these patterns.

In some embodiments, the ambient monitoring device 120 is used for one or more of monitoring health and well-being of elderly adults, monitoring of users with underlying health conditions, monitoring individuals at risk of septic infection, monitoring of Parkinson's disease progression, etc.

In some embodiments, the ambient monitoring device 120 is used to monitor the health and well-being of elderly adults. In one embodiment, the ambient monitoring device 120 is configured to measure various vital signs (e.g., temperature, heart rate, respiratory rate, etc.) of an elderly adult and provide alerts notifying of variations as compared to their measured baseline vital signs. In another embodiment, the ambient monitoring device 120 is configured to monitor activity of an elderly adult and provide alerts notifying of changes (e.g., less frequent movement, slower movement, etc.) as compared to their monitored baseline activity. In another embodiment, the ambient monitoring device 120 is configured to monitor sleep patterns of an elderly adult and provide alerts notifying of changes (e.g., breathing patterns, apnea, etc.) as compared to their monitored baseline sleep patterns. In another embodiment, the ambient monitoring device 120 is configured to monitor various behaviors/routines and provide alerts notifying of changes (e.g., presence in a particular location at a particular time window such as eating meals, sleeping, physical activity, etc.) as compared to their monitored baseline behaviors/routines. In another embodiment, the ambient monitoring device 120 is configured to detect early indicators to potential falls (e.g., measuring vital signs and correlating measurements against known precursors to risk of a fall) or actual falls (e.g., using cm wave radar relying on body models).

In some embodiments, the ambient monitoring device 120 is used to monitor users with underlying health conditions. The ambient monitoring device 120 may monitor pulmonary conditions (e.g., COPD, cystic fibrosis, pneumonia, etc.) by monitoring, for example, changes in respiratory rate, coughing, nature of cough, volume.

The ambient monitoring device 120 may monitor cardiovascular conditions (e.g., heart disease and other heart-related conditions), for example, by monitoring changes in heart rate and heart rate volume.

The ambient monitoring device 120 may be configured to monitor particular vital signs as they relate to conditions associated with cancer treatment (e.g., chemotherapy).

The ambient monitoring device 120 may be configured to monitor particular activity as they relate to conditions associated with dementia and, in particular, progression of the disease (e.g., by monitoring changes in activity or behavior inconsistent with baseline data).

In some embodiments, the ambient monitoring device 120 is used to monitor users at risk of septic infection. The ambient monitoring device 120 may be used to monitor symptoms of sepsis. A fever above 101 degrees F. or below 96.8 degrees F., a detected heart rate higher than 90 bpm, a detected higher breathing rate are all detectable symptoms in that the ambient monitoring device 120 is configured to monitor temperature, heart rate and breathing rate. For example, detection of two or more of the foregoing symptoms alone or in combination with a known recent infectious event may result in an alert being provided to notify of a high risk of a sepsis event. Additional symptoms such as discolored skin patches (e.g., detected via an RGB camera), decreased urination (e.g., detected via lack of presence in a particular location at previously monitored times and frequencies), or a lack of movement may all be used by the ambient monitoring device 120 in addition to the foregoing detected symptoms to suggest a more severe case of a sepsis event.

In some embodiments, the ambient monitoring device 120 is used to monitor Parkinson's disease progression. In one embodiment, the ambient monitoring device 120 is configured to track frequency and intensity of tremors and provide alerts notifying of changes as compared to historical data collected for a particular individual. In another embodiment, the ambient monitoring device 120 is configured to compare monitored changes to known progression precursors and provide alerts notifying of anticipated and suspected disease progression.

The frequency and intensity of tremors may be tracked, for example, using the cmWave radar or the mmWave radar when an individual is within radar range of the ambient monitoring device 120.

In some embodiments, the ambient monitoring device 120 is used for assessment of arterial stiffness. In one embodiment, the ambient monitoring device 120 is comprised of sensors 122 including one or more camera sensors and radar-imaging sensors. A camera sensor may be a high-resolution visible light camera, an infrared imaging sensor or a combination of both. A radar-imaging sensor may employ FMW or impulse radar technology, which may be configured to function in the 60 GHz-100 GHz band to provide high-resolution images and output FMCW or time of flight data and return phase.

When an individual is in close physical proximity to the monitoring device (e.g., 3-5 meters), heart rate and a corresponding waveform may be measured using the radar sensor. For example, in one embodiment, the Doppler and imaging functions of the radar sensor may be utilized to detect a vibration signal of the heart in the chest. Additionally, a pulse wave may be measured using the camera sensor. For example, in one embodiment, remote photoplethysmography (rPPG) may be utilized to detect a pulse wave signal in the forehead, neck or wrists. Using rPPG, the absence or presence of blood in the vessels can be determined and the pleth or pulse profile at a specific location (e.g., the forehead) can be measured accordingly. The phase between these two signals (i.e., the time difference between the peaks in both signals) measured by the foregoing sensors is a direct measure of the time between a contraction of the heart and the moment blood gets into the vessels in the specific location. Thus, the phase represents the time it takes for blood or the pulse wave to go from the heart to the specific location.

In addition to determining the phase, the distance between a specific location of the measured pulse wave (e.g., forehead) and the heart is also determined. In one embodiment, the measured distance may be stored during an initial acquisition of information associated with an individual, whereby each time the individual is in close proximity to the monitoring device, the FMW measuring function may retrieve the previously stored information associated with the recognized individual. An individual may be identified, for example, by a face recognition system to retrieve the previously stored distance information. In another embodiment, when no prior information is stored for an individual, distance may be measured by the monitoring device in real-time. For example, the height of an individual may be estimated through a range measurement function associated with radar and camera sensors, which may use projection equations to help estimate the height of an object from its image in the camera and its range.

Upon obtaining the requisite phase and distance measurements, PWV may be calculated. PWV data may be stored to compile a profile of historical measurements for an individual. The stored PWV data can be retrieved, for example, by a healthcare professional examining changes in arterial stiffness as part of an overall cardiovascular assessment.

It is envisioned that the foregoing monitoring may be deployed in various settings. In one embodiment, the monitoring device may be deployed in an individual's home setting, wherein the PWV measurements may be conducted on preconfigured schedule. For example, the monitoring device may be configured to notify the individual when it is time to measure PWV as part of a daily monitoring routine for assessing heart health, prompting the individual to stand in close proximity to the monitoring device for sensor data acquisition. In another embodiment, the monitoring device may be configured for deployment in an environment where an individual is in a fairly stationary position. For example, the monitoring device may be implemented in a car dashboard to monitor driver health, above hospital beds, a self-service health checkup station, or any other applicable health monitoring setting.

Figure 3A:
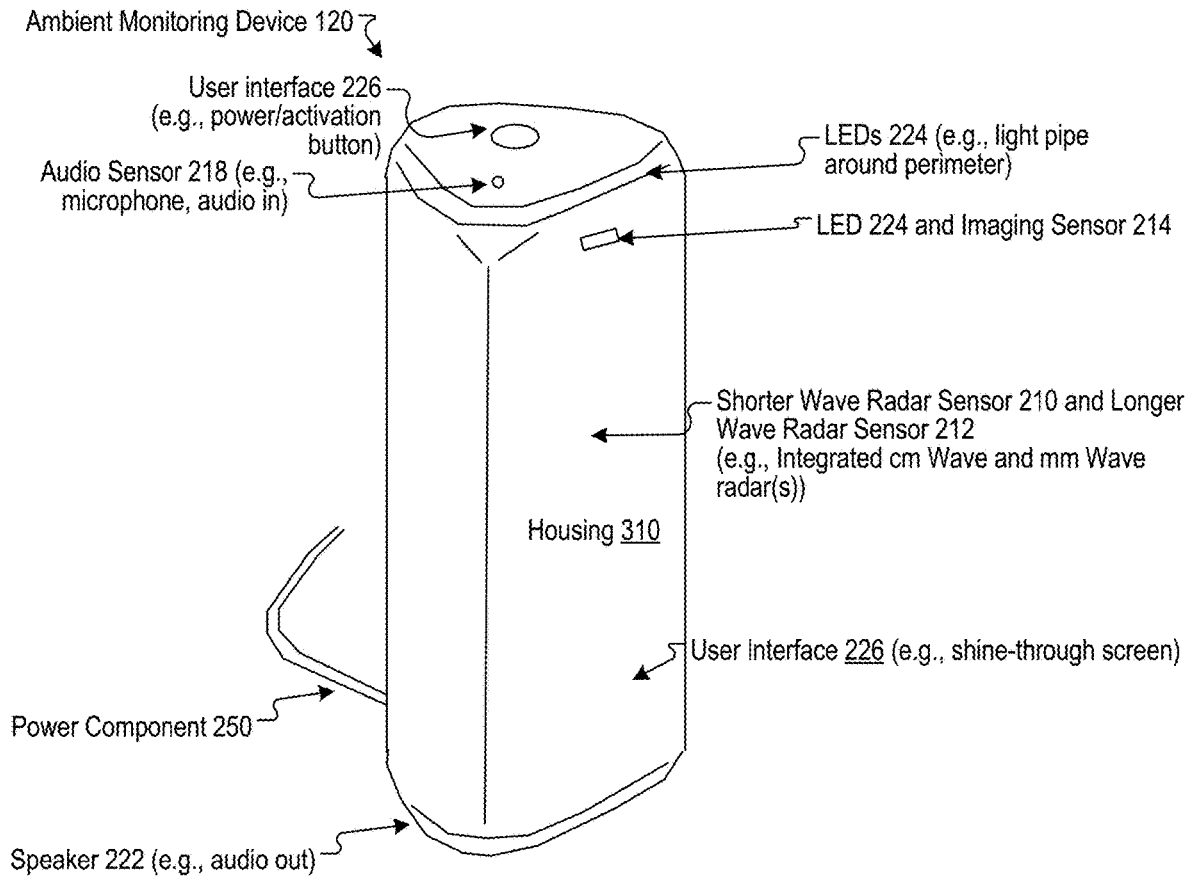
FIG. 3A illustrates an ambient monitoring device, according to certain embodiments.
Figure 3B:
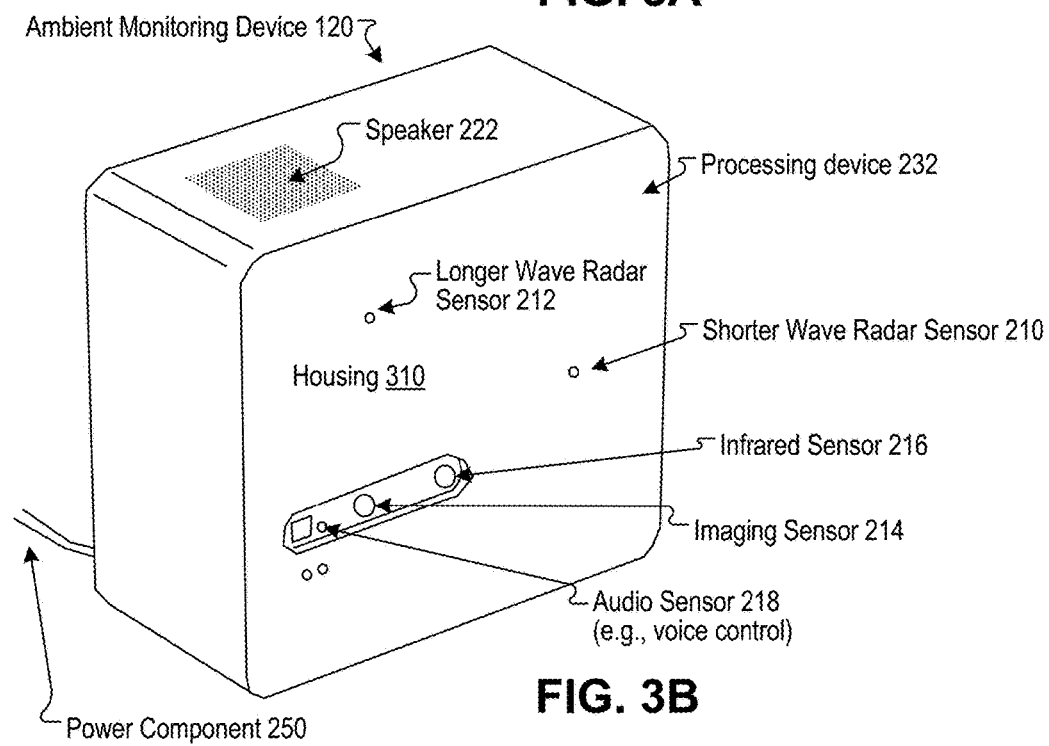
FIG. 3B illustrates an ambient monitoring device, according to certain embodiments.

FIGS. 3A-B illustrate ambient monitoring devices 120, according to certain embodiments. The ambient monitoring devices 120 of FIGS. 3A-B may include one or more features that have similar or same functionality or structure as similarly referenced features of FIG. 2.

The ambient monitoring device 120 may include a housing 310. The ambient monitoring device 120 may include one or more sensors 122, input/output components 220, processing components 230, connectivity components 240, power components 250, and/or debugging components 260 coupled to (e.g., disposed in, attached to, etc.) housing 310.

The sensors 122 may be contactless sensors that provide sensor data of a user that is within a threshold distance (e.g., of the sensor 122 and/or ambient monitoring device 120) without the user contacting the sensor 122 and/or without the user contacting the ambient monitoring device 120. Sensors 122 may include shorter wave radar sensor 210, longer wave radar sensor 212, imagining sensor 214, infrared sensor 216, an audio sensor 218 (e.g., microphone, audio in), and/or the like.

The input/output components 220 may include speaker 222 (e.g., audio out), one or more LEDs 224 (e.g., light pipe around perimeter of the housing 310 proximate the upper surface of the housing 310, RGB LED proximate the imaging sensor 214), one or more user interfaces 226 (e.g., power/activation button at an upper surface of the housing 310, shine-through screen on a sidewall of the housing 310), and/or the like.

The processing components 230 may include processing device 232 and memory 234 that are disposed within the housing 310. The connectivity components 240 may include wireless module 242 and/or cellular module 244 that are disposed within the housing 310. The power components 250 may include a power supply 252. The power components may include an electrical cable to couple the ambient monitoring device 120 to an external power supply. The debugging components 260 may include a communication port 262.

FIG. 4 illustrates a block diagram of an ambient monitoring device 120, according to certain embodiments. Ambient monitoring device 120 includes one or more sensors 212 (e.g., shorter wave radar sensor 210, longer wave radar sensor 212, etc.) that include one or more antennas. For example, the sensors 212 may include at least one Tx antenna and at least two Rx antennas corresponding to the Tx antenna.

Figure 5:
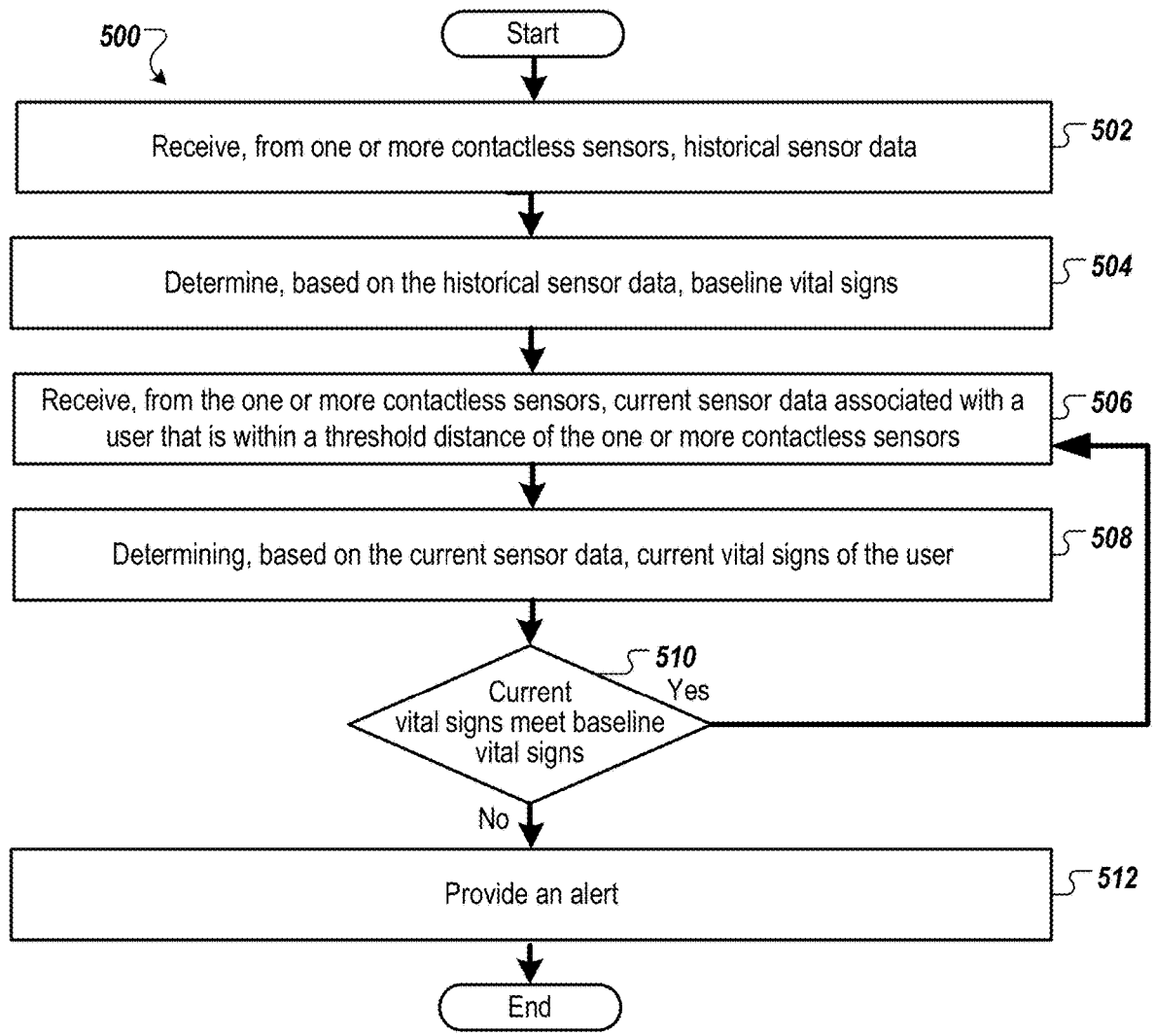
FIG. 5 is a flow diagram associated with an ambient monitoring device, according to certain embodiments.

FIG. 5 is a flow diagram of a method 500 associated with an ambient monitoring device (e.g., ambient monitoring device 120 of one or more of FIGS. 1-4), according to certain embodiments. Method 500 may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In some embodiments, method 500 may be performed, in part, by client device 106 (e.g., ambient monitoring component 108), ambient monitoring device 120 (e.g., ambient monitoring component 108), or predictive server 112 (e.g., predictive component 114). In some embodiments, a non-transitory storage medium stores instructions that when executed by a processing device (e.g., of client device 106, of ambient monitoring device 120, of predictive server 112) cause the processing device to perform method 500.

For simplicity of explanation, method 500 is depicted and described as a series of acts. However, acts in accordance with this disclosure can occur in various orders and/or concurrently and with other acts not presented and described herein. Furthermore, not all illustrated acts may be performed to implement the method 500 in accordance with the disclosed subject matter. In addition, those skilled in the art will understand and appreciate that the method 500 could alternatively be represented as a series of interrelated states via a state diagram or events.

Referring to FIG. 5, at block 502, the processing logic receives, from one or more contactless sensors (e.g., sensors 122), historical sensor data.

At block 504, the processing logic determines, based on the historical sensor data, baseline vital signs. In some embodiments, the historical sensor data is associated with a user being of good health and the baseline vital signs is indicative of an acceptable range of health conditions of a user. In some embodiments, the historical sensor data received from different sensors and the baseline vital signs a combination of the historical sensor data received from the different sensors (e.g., structured data). In some embodiments, the historical sensor data is associated with a state of a user prior to a health condition (e.g., falling, not falling, etc.) and the baseline vital signs is indicative of the health condition of the user that happened after the historical sensor data was received.

At block 506, the processing logic receives, from one or more contactless sensors (e.g., one or more of the contactless sensors from block 502 and/or one or more contactless sensors different from those in block 502), current sensor data associated with a user that is within a threshold distance of the one or more contactless sensors.

In some embodiments, the processing logic determines an indoor space (e.g., a room, an apartment, etc.) based on the historical sensor data and the processing logic determines movements of the user in the indoor space based on the current sensor data. In some embodiments, the processing logic determines movements of the user based on shorter wave sensor data (e.g., first subset of the current sensor data) and longer wave sensor data (e.g., second subset of the current sensor data).

At block 508, the processing logic determines based on the current sensor data, current vital signs of the user. In some embodiments, the current sensor data includes a first subset from a first contactless sensor and a second subset from a second contactless sensor and the processing logic combines the first subset and the second subset to form structured data. The current vital signs may be based on the structured data.

At block 510, the processing logic determines whether the current vital signs meet baseline vital signs. Responsive to the current vital signs meeting the baseline vital signs, the method continues to block 506 (e.g., to continue monitoring). Responsive to the current vital signs not meeting the baseline vital signs, the method continues to block 512.

In some embodiments, the processing device determines at least a portion fo the historical sensor data corresponds to a user, determines at least a portion of the current sensor data corresponds to the user, and, at block 506, determines whether the current vital signs associated with the at least a portion fo the current sensor data meet the baseline vital signs associated with the at least a portion fo the historical sensor data (e.g., determine whether the vital signs of the user have changed more than a threshold amount).

In some embodiments, the processing logic receives user input indicative of a health condition of a user and determines based on the user input, whether the current vital signs meet the baseline vital signs.

Figure 7A:
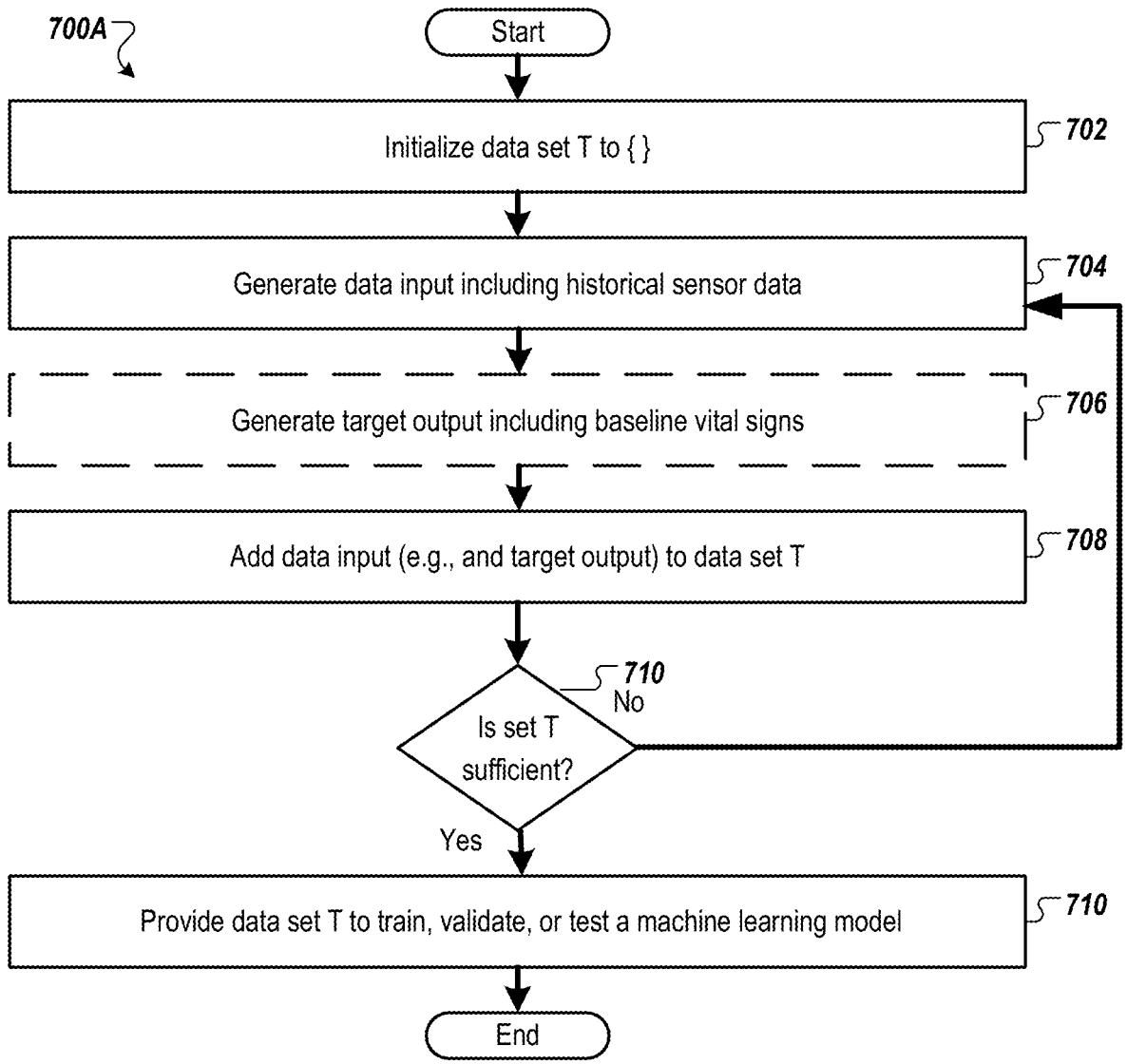
FIGS. 7A-C are flow diagrams of methods associated with generating predictive data, according to certain embodiments.
Figure 7B:
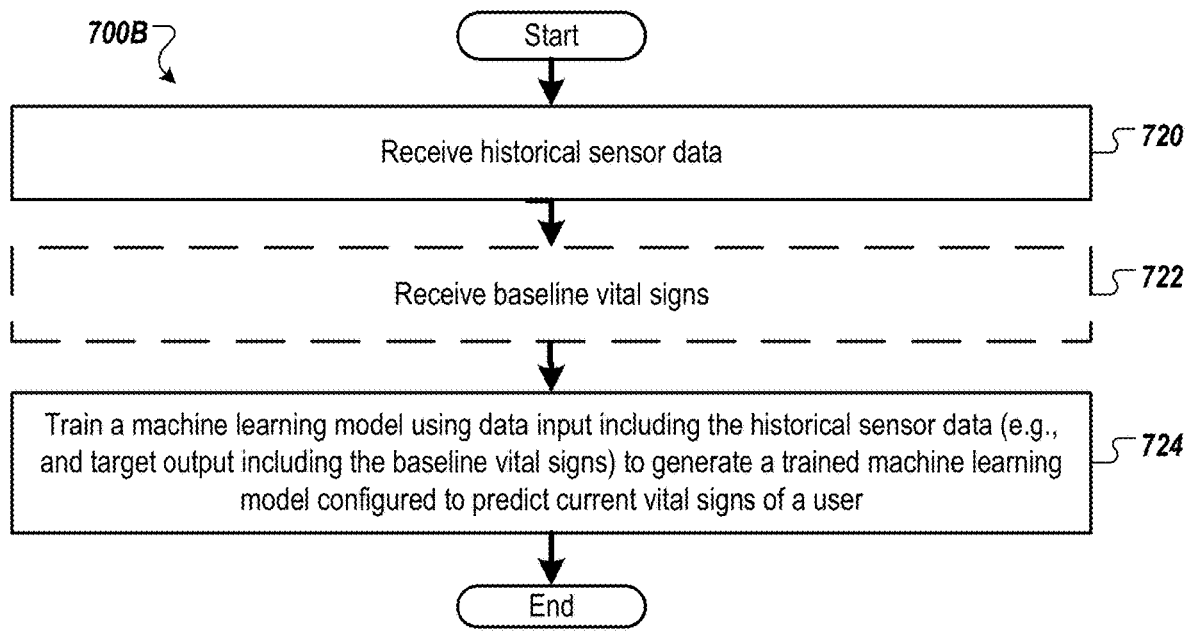
Figure 7C:
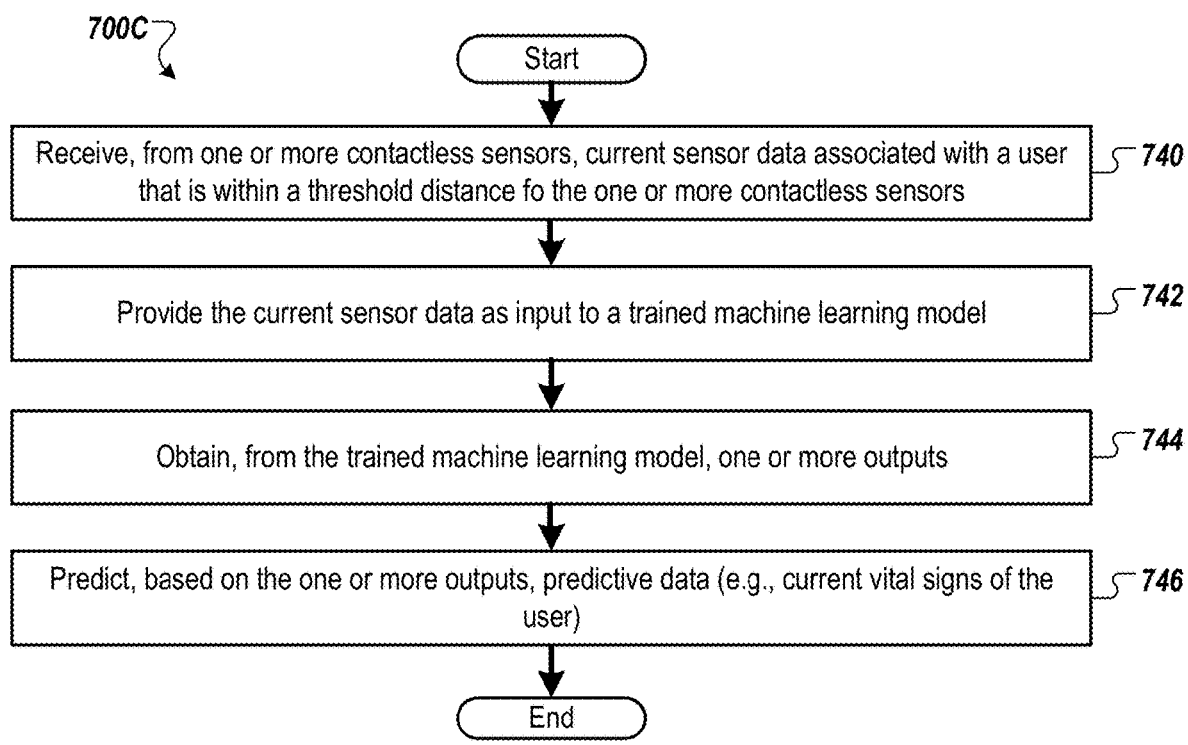

In some embodiments, the processing logic determines the current vital signs and/or determines whether the current vital signs meet the baseline vital signs based on a trained machine learning model (e.g., see FIGS. 7A-C).

At block 512, the processing logic causes an alert to be provided. In some embodiments, the processing logic causes an alert to be provided via an input/output component (e.g., speaker, user interface, etc.) of the ambient monitoring device. In some embodiments, the processing logic transmits data to a remote device (e.g., client device, health provider device, etc.) to cause the remote device to display an alert.

Figure 6A:
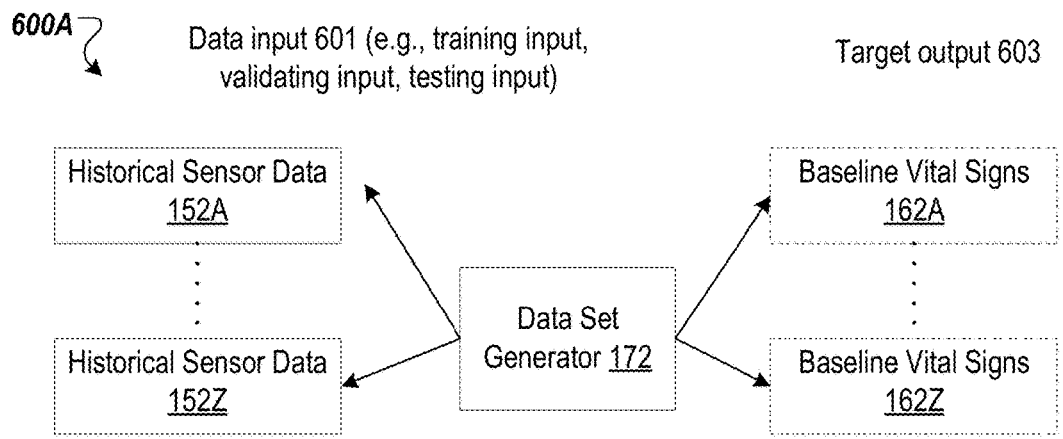
FIG. 6A is an example data set generator to create data sets for a model, according to certain embodiments.

FIG. 6A is an example data set generator 172 to create data sets for a model (e.g., model 190 of FIG. 1), according to certain embodiments. In some embodiments, the data set generator 172 uses historical data (e.g., historical sensor data 152 and/or baseline vital signs 162). System 600A of FIG. 6A shows data set generator 172, data inputs 601, and target output 603.

In some embodiments, data set generator 172 generates a data set (e.g., training set, validating set, testing set) that includes one or more data inputs 601 (e.g., training input, validating input, testing input) and/or target outputs 602. Data inputs 601 may also be referred to as "features," "attributes," or information." In some embodiments, data set generator 172 may provide the data set to the training engine 182, validating engine 184, or testing engine 186, where the data set is used to train, validate, or test the model 190. Some embodiments of generating a training set may further be described with respect to FIG. 7A.

In some embodiments, data set generator 172 generates the data input 601 based on historical data. In some embodiments, data inputs 601 may include one or more sets of features for the historical data. Each instance of historical data may include historical sensor data 152 from one or more types of sensors (e.g., associated with one or more users). Each instance of historical data may include baseline vital signs 162 (e.g., associated with the one or more users).

In some embodiments, data set generator 172 may generate a first data input corresponding to a first set of features to train, validate, or test a first model and the data set generator 172 may generate a second data input corresponding to a second set of features to train, validate, or test a second model.

In some embodiments, the data set generator 172 may discretize the data input 601 (e.g., to use in classification algorithms for regression problems). Discretization of the data input 601 may transform continuous values of variables into discrete values. In some embodiments, the discrete values for the data input 601 indicate discrete users.

Data inputs 601 to train, validate, or test a model may include information for a particular user or for multiple users.

In some embodiments, subsequent to generating a data set and training, validating, or testing model 190 using the data set, the model 190 may be further trained, validated, or tested (e.g., further historical data, further current data) or adjusted (e.g., adjusting weights associated with input data of the model 190, such as connection weights in a neural network).

Figure 6B:
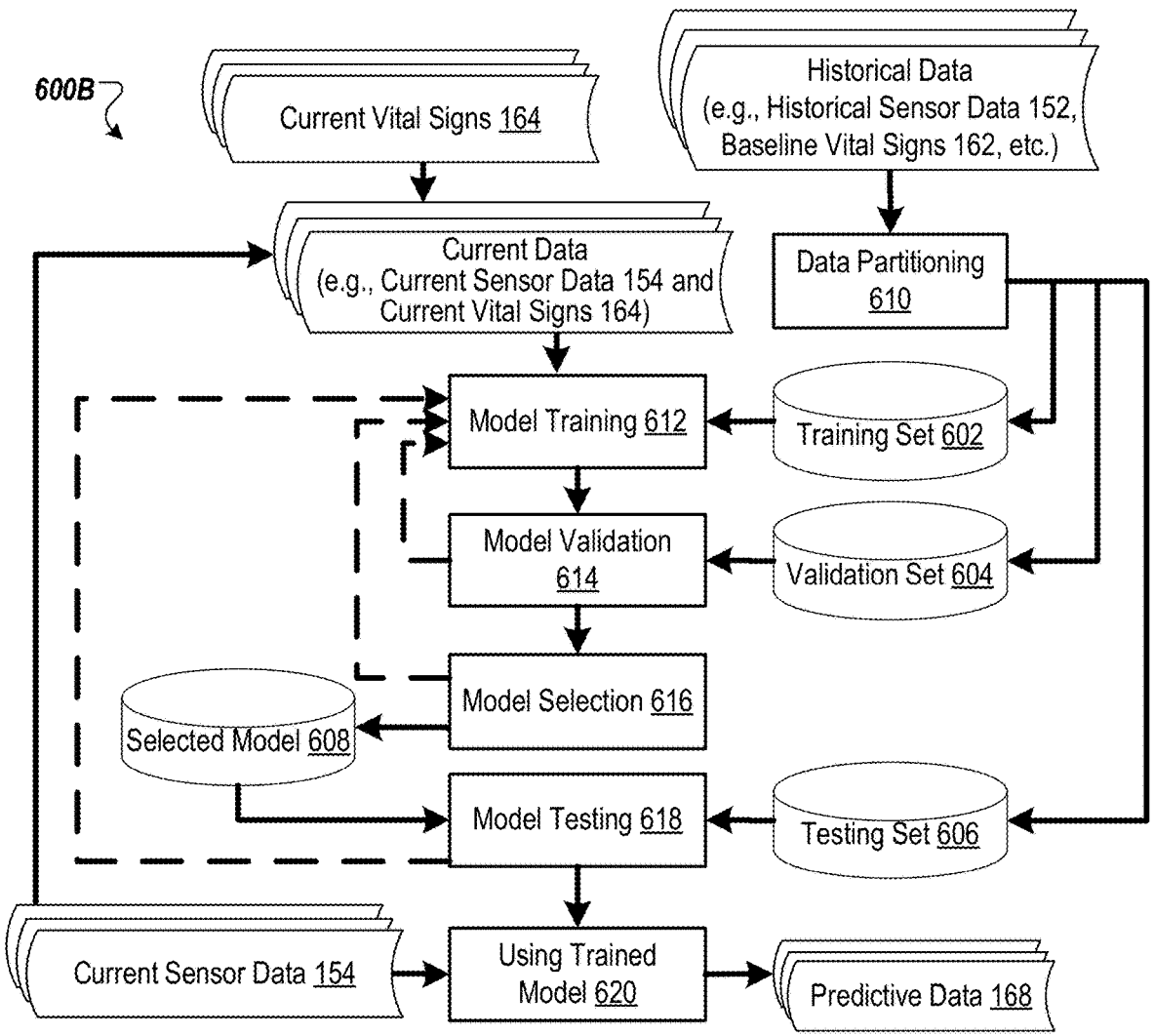
FIG. 6B is a block diagram illustrating determining predictive data, according to certain embodiments.

FIG. 6B is a block diagram illustrating a system 600B for generating predictive data 168, according to certain embodiments. The system 600B may be used to determine a corrective action (e.g., provide an alert, etc.) based on historical sensor data 152 and/or baseline vital signs 162.

At block 610, the system 600 (e.g., predictive system 110 of FIG. 1) performs data partitioning (e.g., via data set generator 172 of server machine 170 of FIG. 1) of the historical data (e.g., historical sensor data 152, baseline vital signs 162) to generate the training set 602, validation set 604, and testing set 606. For example, the training set may be 60% of the historical data, the validation set may be 20% of the historical data, and the validation set may be 20% of the historical data. The system 600 may generate a plurality of sets of features for each of the training set, the validation set, and the testing set. In some examples, if the historical sensor data 152 is associated with 10 sensors (e.g., sensors 122 of FIG. 1) and 20 users (e.g., users that each correspond to the sensor data from the 10 sensors), a first set of features may be sensors 1-5, a second set of features may be sensors 6-10, the training set may be users 1-6, the validation set may be users 7-8, and the testing set may be users 9-10. In this example, the first set of features of the training set would be from sensors 1-4 for users 1-6.

At block 612, the system 600 performs model training (e.g., via training engine 182 of FIG. 1) using the training set 602. The system 600 may train multiple models using multiple sets of features of the training set 602 (e.g., a first set of features of the training set 602, a second set of features of the training set 602, etc.). For example, system 600 may train a model to generate a first trained model using the first set of features in the training set (e.g., sensor data from sensors 1-5 for users 1-6) and to generate a second trained model using the second set of features in the training set (e.g., sensor data from sensors 6-10 for users 1-6). In some embodiments, the first trained model and the second trained model may be combined to generate a third trained model (e.g., which may be a better predictor than the first or the second trained model on its own). In some embodiments, sets of features used in comparing models may overlap (e.g., first set of features being from sensors 1-7 and second set of features being from sensors 5-10). In some embodiments, hundreds of models may be generated including models with various permutations of features and combinations of models.

At block 614, the system 600 performs model validation (e.g., via validation engine 184 of FIG. 1) using the validation set 604. The system 600 may validate each of the trained models using a corresponding set of features of the validation set 604. For example, system 600 may validate the first trained model using the first set of features in the validation set (e.g., sensor data from sensors 1-5 for users 7-8) and the second trained model using the second set of features in the validation set (e.g., sensor data from sensors 6-10 for users 7-8). In some embodiments, the system 600 may validate hundreds of models (e.g., models with various permutations of features, combinations of models, etc.) generated at block 612. At block 614, the system 600 may determine an accuracy of each of the one or more trained models (e.g., via model validation) and may determine whether one or more of the trained models has an accuracy that meets a threshold accuracy. Responsive to determining that none of the trained models has an accuracy that meets a threshold accuracy, flow returns to block 612 where the system 600 performs model training using different sets of features of the training set. Responsive to determining that one or more of the trained models has an accuracy that meets a threshold accuracy, flow continues to block 616. The system 600 may discard the trained models that have an accuracy that is below the threshold accuracy (e.g., based on the validation set).

At block 616, the system 600 performs model selection (e.g., via selection engine 185 of FIG. 1) to determine which of the one or more trained models that meet the threshold accuracy has the highest accuracy (e.g., the selected model 608, based on the validating of block 614). Responsive to determining that two or more of the trained models that meet the threshold accuracy have the same accuracy, flow may return to block 612 where the system 600 performs model training using further refined training sets corresponding to further refined sets of features for determining a trained model that has the highest accuracy.

At block 618, the system 600 performs model testing (e.g., via testing engine 186 of FIG. 1) using the testing set 606 to test the selected model 608. The system 600 may test, using the first set of features in the testing set (e.g., sensor data from sensors 1-5 for users 9-10), the first trained model to determine the first trained model meets a threshold accuracy (e.g., based on the first set of features of the testing set 606). Responsive to accuracy of the selected model 608 not meeting the threshold accuracy (e.g., the selected model 608 is overly fit to the training set 602 and/or validation set 604 and is not applicable to other data sets such as the testing set 606), flow continues to block 612 where the system 600 performs model training (e.g., retraining) using different training sets corresponding to different sets of features (e.g., sensor data from different sensors). Responsive to determining that the selected model 608 has an accuracy that meets a threshold accuracy based on the testing set 606, flow continues to block 620. In at least block 612, the model may learn patterns in the historical data to make predictions and in block 618, the system 600 may apply the model on the remaining data (e.g., testing set 606) to test the predictions.

At block 620, system 600 uses the trained model (e.g., selected model 608) to receive current sensor data 154 and determines (e.g., extracts), from the output of the trained model, predictive data 168 to perform corrective actions (e.g., provide an alert).

In some embodiments, one or more operations of the blocks 610-620 may occur in various orders and/or with other operations not presented and described herein. In some embodiments, one or more operations of blocks 610-620 may not be performed. For example, in some embodiments, one or more of data partitioning of block 610, model validation of block 614, model selection of block 616, or model testing of block 618 may not be performed.

FIGS. 7A-C are flow diagrams of methods 700A-C associated with generating predictive data, according to certain embodiments. Methods 700A-C may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In some embodiments, method 700A may be performed, in part, by predictive system 110 (e.g., server machine 170, data set generator 172, etc.). Predictive system 110 may use method 700A to at least one of train, validate, or test a model, in accordance with embodiments of the disclosure. In some embodiments, one or more operations of method 700A may be performed by data set generator 172 of server machine 170 as described with respect to FIGS. 1 and 6A. In some embodiments, methods 700B-C may be performed, in part, by predictive system 110 (e.g., predictive server 112, predictive component 114, etc.). Predictive system 110 may use method 700B to train a model, in accordance with embodiments of the disclosure. Predictive system 110 may use method 700C to use a trained model, in accordance with embodiments of the disclosure. In some embodiments, one or more operations of methods 700B-C may be performed by predictive component 114 of predictive server 112 as described with respect to FIGS. 1 and 6B. It may be noted that components described with respect to one or more of FIGS. 1-6B may be used to illustrate aspects of FIGS. 7A-C. In some embodiments, a non-transitory storage medium stores instructions that when executed by a processing device (e.g., of predictive system 110) cause the processing device to perform methods 700A-C.

For simplicity of explanation, methods 700A-C are depicted and described as a series of acts. However, acts in accordance with this disclosure can occur in various orders and/or concurrently and with other acts not presented and described herein. Furthermore, not all illustrated acts may be performed to implement the methods 700A-C in accordance with the disclosed subject matter. In addition, those skilled in the art will understand and appreciate that the methods 700A-C could alternatively be represented as a series of interrelated states via a state diagram or events.

Referring to FIG. 7A, method 700A is associated with generating a data set for a model for determining predictive data (e.g., for performing a corrective action).

At block 702 the processing logic implementing method 700A initializes a training set T to an empty set.

At block 704, processing logic generates first data input (e.g., first training input, first validating input) that includes historical data (e.g., historical sensor data 152 of FIG. 1). In some embodiments, the first data input may include a first set of features for types of historical data and a second data input may include a second set of features for types of historical data (e.g., as described with respect to FIG. 6A). The processing logic may generate the data input based on portions of the historical data (e.g., from specific sensors, associated with specific users, etc.).

In some embodiments, at block 706, processing logic generates target output that includes baseline vital signs (e.g., associated with the historical sensor data 152).

At block 708, processing logic adds the data input generated at block 704 (e.g., and target output from block 706) to data set T.

At block 710, processing logic branches based on whether data set T is sufficient for at least one of training, validating, and/or testing model 190. If so, execution proceeds to block 712, otherwise, execution continues back at block 704. In some embodiments, the sufficiency of data set T may be determined based simply on the amount of data in the data set, while in some other implementations, the sufficiency of data set T may be determined based on one or more other criteria (e.g., a measure of diversity of the data examples, accuracy, etc.) in addition to, or instead of, the amount of data in the data set.

At block 710, processing logic provides data set T (e.g., to server machine 180) to train, validate, and/or test model 190. In some embodiments, data set T is a training set and is provided to training engine 182 of server machine 180 to perform the training. In some embodiments, data set T is a validation set and is provided to validation engine 184 of server machine 180 to perform the validating. In some embodiments, data set T is a testing set and is provided to testing engine 186 of server machine 180 to perform the testing. In the case of a neural network, for example, input values (e.g., numerical values associated with data inputs 601) are input to the neural network. The connection weights in the neural network are then adjusted in accordance with a learning algorithm (e.g., back propagation, etc.), and the procedure is repeated for the other input/output mappings in data set T. After block 710, model (e.g., model 190) can be at least one of trained using training engine 182 of server machine 180, validated using validating engine 184 of server machine 180, or tested using testing engine 186 of server machine 180. The trained model may be implemented by predictive component 114 (of predictive server 112) to generate predictive data 168 (e.g., for performing corrective action, for providing alerts, etc.).

Referring to FIG. 7B, method 700B is associated with training a model for determining predictive data (e.g., for performing a corrective action).

At block 720, processing logic identifies historical sensor data from contactless sensors (e.g., of one or more ambient monitoring devices). The historical data sensor may correspond to one or more users, one or more contactless sensors, and/or one or more ambient monitoring devices.

In some embodiments, at block 722, processing logic identifies baseline vital signs associated with the historical sensor data (e.g., associated with the same users).

In some embodiments, the historical sensor data of block 720 is a surface temperature of a user, a heart rate of the user, and/or vascular pleth waveform of the user and the baseline vital signs (e.g., historical vital signs) of block 722 is core temperature of the user.

In some embodiments, the historical sensor data of block 720 is associated with positions (e.g., standing, sitting, laying down, etc.) and/or movements (e.g., standing up, sitting down, falling, walking, running, etc.) of a user. The historical sensor data may be received from a first type of sensor, such as a high accuracy visual stereoscopic sensor mounted to the ambient monitoring device 120 and/or one or more radar sensors (e.g., shorter wave radar sensor 210 and/or longer wave radar sensor 212). The baseline vital signs of block 722 may be the position and/or movement that occurred responsive to the historical sensor data. In some embodiments, the baseline vital signs may be input via user input (e.g., audio input, text input, etc.) indicative of the position and/or movement that occurred. In some embodiments, the baseline vital signs may be determined by processing the historical sensor data. In some embodiments, the baseline vital signs may be determined based on a first subset of the historical sensor data (e.g., from a visual stereoscopic sensor) and the baseline vital signs may be based on a second subset of the historical sensor data (e.g., from shorter wave radar sensor 210 and/or longer wave radar sensor 212). In some embodiments, the current sensor data that is input into the trained machine learning model is from different sensors (e.g., one or more radar sensors, such as shorter wave radar sensor 210 and/or longer wave radar sensor 212) than the first sensor (e.g., high accuracy visual stereoscopic sensor mounted to the ambient monitoring device 120) that provided the historical sensor data.

In some embodiments, the baseline vital signs is a historical vital sign indicative of a health condition of a user responsive to the historical sensor data. For example, the historical vital sign may be falling responsive to historical sensor data that occurred prior to the fall. The machine learning model may be trained to detect patterns (e.g., in sensor data) that are precursors to health problems (e.g., vital signs).

At block 724, processing logic trains a model using data input including the historical data to generate a trained model configured to generate predictive data (e.g., to cause performance of a corrective action).

In some embodiments, the predictive data indicates a predictive core temperature of the user. In some embodiments, the predictive data indicates a predictive position and/or movement.

In some embodiments, the model is trained based on data input (e.g., without target output) to generate an unsupervised trained model (e.g., to cluster data). In some embodiments, the model is trained based on data input and target output to generate a supervised trained model.

Referring to FIG. 7C, method 700C is associated with using a model for determining predictive data (e.g., for performing a corrective action).

At block 740, processing logic receives current sensor data from one or more contactless sensors.

At block 742, processing logic provides the current sensor data as input to a trained machine learning model (e.g., the trained machine learning model from block 724 of FIG. 7B).

At block 744, processing logic obtains, from the trained machine learning model, one or more outputs.

At block 746, processing logic predicts, based on the one or more outputs, predictive data. In some embodiments, the predictive data includes current vital signs of the user. In some embodiments, the predictive data includes an alert associated with the user.

In some embodiments, the current sensor data includes surface temperature of a user, a heart rate of the user, and/or vascular pleth waveform of the user and the current vital signs (e.g., predictive vital signs) is core temperature of the user.

In some embodiments, the current sensor data is associated with positions (e.g., standing, sitting, laying down, etc.) and/or movements (e.g., standing up, sitting down, falling, walking, running, etc.) of a user and the current vital signs (e.g., predictive vital signs) is the position and/or movement (e.g., a predictive fall).

Figure 8:
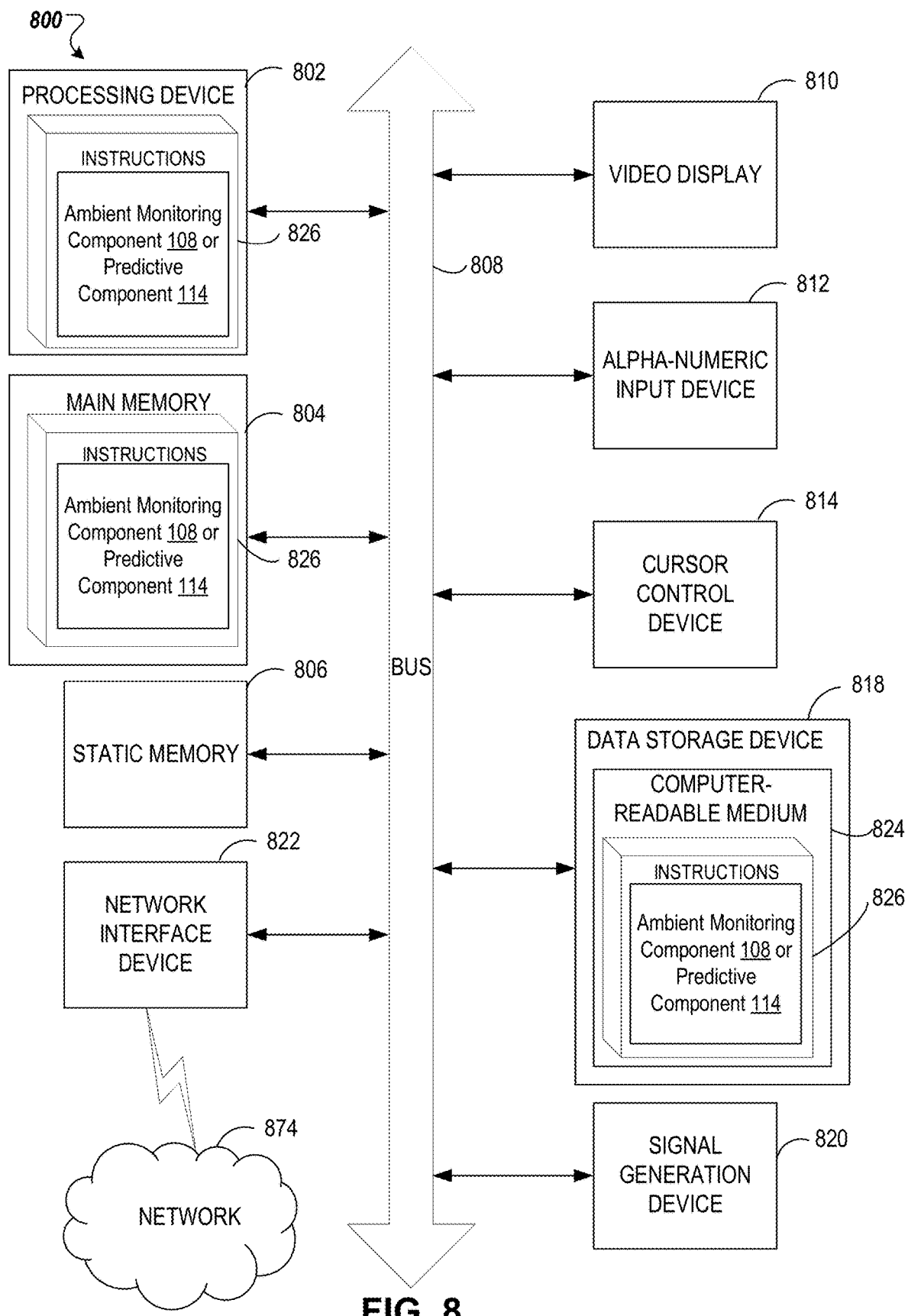
FIG. 8 is a block diagram illustrating a computer system, according to certain embodiments.

FIG. 8 is a block diagram illustrating a computer system 800, according to certain embodiments. In some embodiments, computer system 800 may be connected (e.g., via a network, such as a Local Area Network (LAN), an intranet, an extranet, or the Internet) to other computer systems. Computer system 800 may operate in the capacity of a server or a client computer in a client-server environment, or as a peer computer in a peer-to-peer or distributed network environment. Computer system 800 may be provided by a PC, a tablet PC, a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein. In some embodiments, computer system 800 is one or more of client device 106, ambient monitoring device 120, etc. In some embodiments, computer system 800 includes less components than those shown in FIG. 8. In some embodiments, computer system 800 includes more components than those shown in FIG. 8.

In a further aspect, the computer system 800 may include a processing device 802, a volatile memory 804 (e.g., random access memory (RAM)), a non-volatile memory 806 (e.g., read-only memory (ROM) or electrically-erasable programmable ROM (EEPROM)), and a data storage device 816, which may communicate with each other via a bus 808.

Processing device 802 may be provided by one or more processors such as a general purpose processor (such as, for example, a complex instruction set computing (CISC) microprocessor, a reduced instruction set computing (RISC) microprocessor, a very long instruction word (VLIW) microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Computer system 800 may further include a network interface device 822. Computer system 800 also may include a video display unit 810 (e.g., a liquid crystal display (LCD)), an alphanumeric input device 812 (e.g., a keyboard), a cursor control device 814 (e.g., a mouse), and a signal generation device 820.

In some implementations, data storage device 816 may include a non-transitory computer-readable storage medium 824 on which may store instructions 826 encoding any one or more of the methods or functions described herein, including instructions encoding components of FIG. 1 (e.g., ambient monitoring component 108, predictive component 114, etc.) and for implementing methods described herein.

Instructions 826 may also reside, completely or partially, within volatile memory 804 and/or within processing device 802 during execution thereof by computer system 800, hence, volatile memory 804 and processing device 802 may also constitute machine-readable storage media.

While computer-readable storage medium 824 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

Unless specifically stated otherwise, terms such as "receiving," "determining," "providing," "combining," "training," "obtaining," "predicting," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. Also, the terms "first," "second," "third," "fourth," etc. as used herein are meant as labels to distinguish among different elements and may not have an ordinal meaning according to their numerical designation.

Examples described herein also relate to an apparatus for performing the methods described herein. This apparatus may be specially constructed for performing the methods described herein, or it may include a general purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods described herein and/or each of their individual functions, routines, subroutines, or operations. Examples of the structure for a variety of these systems are set forth in the description above.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

Embodiments also relate to an apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the present invention as described herein. It should also be noted that the terms "when" or the phrase "in response to," as used herein, should be understood to indicate that there may be intervening time, intervening events, or both before the identified operation is performed.

Various operations are described as multiple discrete operations, in turn, in a manner that is most helpful in understanding the present disclosure, however, the order of description should not be construed to imply that these operations are necessarily order dependent. In particular, these operations need not be performed in the order of presentation.

The terms "over," "under," "between," "disposed on," and "on" as used herein refer to a relative position of one material layer or component with respect to other layers or components. For example, one layer disposed on, over, or under another layer may be directly in contact with the other layer or may have one or more intervening layers. Moreover, one layer disposed between two layers may be directly in contact with the two layers or may have one or more intervening layers. Similarly, unless explicitly stated otherwise, one feature disposed between two features may be in direct contact with the adjacent features or may have one or more intervening layers.

Various embodiments can have different combinations of the structural features described above. For instance, all optional features of a vehicle whip system described above can also be implemented in a vehicle whip system and specifics in the examples can be used anywhere in one or more embodiments.

While the present disclosure has been described with respect to a limited number of embodiments, those skilled in the art will appreciate numerous modifications and variations therefrom. It is intended that the appended claims cover all such modifications and variations as fall within the true spirit and scope of this present disclosure.

In the description herein, numerous specific details are set forth, such as examples of specific types of material, specific sizes, specific surfaces, specific structures, specific details, specific configurations, specific types, specific system components, specific operations, specific electrical connection types, etc. in order to provide a thorough understanding of the present disclosure. It will be apparent, however, to one skilled in the art that these specific details need not be employed to practice the present disclosure. In other instances, well known components or methods, such as specific and alternative material, sizes, surfaces, structures, details, configurations, types, system components, operations, electrical connection types, etc. have not been described in detail in order to avoid unnecessarily obscuring the present disclosure. In some embodiments, one or more of the dimensions described herein may be varied by +/−1%. In some embodiments, one or more of the dimensions described herein may be varied by +/−5%. In some embodiments, one or more of the dimensions described herein may be varied by +/−10%. In some embodiments, one or more of the dimensions described herein may be varied by +/−15%. In some embodiments, one or more of the dimensions described herein may be varied by +/−20%. In some embodiments, one or more of the dimensions described herein may not be used.

Although some of the embodiments herein are described with reference to LED and vehicles (e.g., and spare-tire mounts of vehicles), other embodiments are applicable to other types of light emitting devices, illuminating devices, electrical devices, objects and/or mounting surfaces. Although some of the embodiments herein are described with reference to a flag whip (e.g., coupled to a vehicle), other embodiments are applicable to other types of structures, such as a flagless whip, a component coupled to a vehicle, a component (e.g., flag whip) coupled to something that is not a vehicle, a component that conventionally has an exterior control wires, or the like. Similar techniques and teachings of embodiments of the present disclosure can be applied to other types of components, devices, systems, and assemblies (e.g., that mount in different planes to two objects, that have exterior control wires, etc.). In addition, the description herein provides examples, and the accompanying drawings show various examples for the purposes of illustration. However, these examples should not be construed in a limiting sense as they are merely intended to provide examples of embodiments of the present disclosure rather than to provide an exhaustive list of all possible implementations of embodiments of the present disclosure.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task.

Furthermore, use of the phrases 'to,' 'capable of/to,' and or 'operable to,' in one embodiment, refers to some apparatus, hardware, and/or element designed in such a way to enable use of the apparatus, hardware, and/or element in a specified manner. Note that use of to, capable to, or operable to, in one embodiment, refers to the latent state of an apparatus, hardware, and/or element, where the apparatus, hardware, and/or element is not operating but is designed in such a manner to enable use of an apparatus in a specified manner.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

In the foregoing specification, a detailed description has been given with reference to specific exemplary embodiments. It will, however, be evident that various modifications and changes can be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but can refer to different and distinct embodiments, as well as potentially the same embodiment.

The words "example" or "exemplary" are used herein to mean serving as an example, instance or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and can not necessarily have an ordinal meaning according to their numerical designation.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

What is claimed is:

1. An ambient monitoring device comprising:
   a plurality of contactless sensors, the plurality of contactless sensors comprising at least a millimeter wave (mmWave) radar sensor and a remote photoplethysmography (rPPG) enabled camera sensor;
   a processing device coupled to the plurality of contactless sensors, wherein the processing device is configured to:
      receive, from at least one sensor of the plurality of contactless sensors, data associated with a user that is located within a threshold distance of the ambient monitoring device, wherein the at least one sensor does not make physical contact with the user;
      determine a current vital sign of the user located within the threshold distance by deriving the current vital sign in part from a pleth waveform generated by the rPPG enabled camera sensor and point cloud data generated by the mmWave radar sensor; and
      generate an alert responsive to a determination that the current vital sign does not meet an acceptable measure, wherein the determination is based at least in part on a corresponding baseline vital sign measurement derived from historical sensor data associated with the user.

2. The ambient monitoring device of claim 1, wherein the current vital sign comprises one of:
   a heart rate;
   a breathing rate;
   a body temperature;
   a body movement;
   a body position;
   a user activity in ambient surroundings;
   a hydration level;
   a blood pressure; or
   a change in skin color tone.

3. The ambient monitoring device of claim 1, wherein the processing device is further configured to communicate the alert via one or more of an audio component of the ambient monitoring device, a user interface of the ambient monitoring device, or a computing device remote from the ambient monitoring device.

4. The ambient monitoring device of claim 1, wherein the plurality of contactless sensors comprise one or more of:
   a high-resolution visible light camera;
   an infrared imaging sensor;
   a motion radar imaging sensor;
   a microphone array sensor;
   a vibration sensor;
   an accelerometer sensor;
   a depth sensor;
   an ambient temperature sensor; or
   an ambient humidity sensor.

5. The ambient monitoring device of claim 1, wherein data received from the plurality of sensors comprises a first data subset from a first contactless sensor and a second data subset from a second contactless sensor, wherein the processing device is further configured to combine the first data subset and the second data subset to form structured data, and wherein the current vital sign is based on the structured data.

6. The ambient monitoring device of claim 1, wherein the processing device is further configured to:
   determine an indoor space based on the historical sensor data; and
   determine movements of the user in the indoor space based on the data received from the at least one sensor.

7. The ambient monitoring device of claim 6, wherein a first subset of the data received from the at least one sensor comprises short wave radar sensor data and a second subset of the data received from the at least one sensor comprises long wave radar sensor data, and wherein the processing device is configured to determine the movements of the user based on the short wave radar sensor data and the long wave radar sensor data.

8. The ambient monitoring device of claim 1, wherein the processing device is further configured to:
   receive user input indicative of a health condition of the user; and
   determine, based on the user input, whether the current vital sign meets an acceptable measure associated with the health condition.

9. The ambient monitoring device of claim 1, wherein the processing device is further configured to:
   provide the data received from the at least one sensor as input to a trained machine learning model; and
   receive a prediction of whether the current vital sign meets the corresponding baseline vital sign based at least in part on one or more outputs of the trained machine learning model.

* * * * *